(12) United States Patent
Lio et al.

(10) Patent No.: US 8,410,282 B2
(45) Date of Patent: Apr. 2, 2013

(54) COMPOUNDS AS ADENOSINE $A_1$ RECEPTOR ANTAGONISTS

(75) Inventors: Lyhen Gonzalez Lio, Llinars del Vallès (ES); Juan Alberto Camacho Gomez, Llinars del Vallès (ES)

(73) Assignee: Palobiofarma, S.L., Llinars del Valles (ES)

( * ) Notice: Subject to any disclaimer, the term of this patent is extended or adjusted under 35 U.S.C. 154(b) by 188 days.

(21) Appl. No.: 12/679,941

(22) PCT Filed: Sep. 30, 2008

(86) PCT No.: PCT/IB2008/002556
§ 371 (c)(1),
(2), (4) Date: May 19, 2010

(87) PCT Pub. No.: WO2009/044250
PCT Pub. Date: Apr. 9, 2009

(65) Prior Publication Data
US 2010/0311703 A1    Dec. 9, 2010

(30) Foreign Application Priority Data

Oct. 2, 2007    (ES) .................................. 200702643

(51) Int. Cl.
C07D 277/00    (2006.01)
C07D 293/00    (2006.01)
C07D 413/00    (2006.01)
C07D 285/08    (2006.01)
C07D 213/55    (2006.01)

(52) U.S. Cl. ........ 548/195; 548/100; 548/125; 548/128; 546/342

(58) Field of Classification Search .................. 548/100, 548/125, 128, 195; 546/342
See application file for complete search history.

(56) References Cited

U.S. PATENT DOCUMENTS

2005/0004134 A1    1/2005    Tsutsumi et al.
2005/0153977 A1*   7/2005    Sugasawa et al. ....... 514/254.02

FOREIGN PATENT DOCUMENTS

WO    WO 2007/116106    10/2007

OTHER PUBLICATIONS

Tilburg, Van E. W. et al., Substituted 4-Phenyl-2-(phenylcarboxamido)-1, 3-thiazole derivatives as antagonists for the Adenosine A1 receptor, Bioorganic & Medicinal Chemistry Letters, Pergamon, Elsevier Science, GB, vol. 11, Jan. 1, 2001, pp. 2017-2019.

Muijlwijk-Koezen Van J. E. et al., Thiazole and Thiadiazole Analogues as a Novel class of Adenosine Receptor Antagonists, Jornal of Medicinal Chemistry, US American Chemical Society, vol. 44, No. 5, Mar. 1, 2001, pp. 749-762.

* cited by examiner

*Primary Examiner* — Shirley V Gembeh
(74) *Attorney, Agent, or Firm* — Leason Ellis LLP

(57) ABSTRACT

This compounds correspond to the formula (I), where: $R^1$ represents and aryl or heteroaryl group optionally substituted by one or more substituents selected from the group consisting of halogen atoms, straight or branched optionally substituted lower alkyl, cycloalkyl, hydroxy, straight or branched, optionally substituted lower alkoxy, cyano, or —$CO_2R'$, wherein R' represents a hydrogen atom or a straight or branched, optionally substituted lower alkyl group; $R^2$ represents a group selected from: a) a straight or branched lower alkyl group substituted by one or more carboxylic groups (—COOH) and optionally substituted by one or more halogen atoms; b) a cycloalkyl group substituted by one or more carboxylic groups (—COOH) and optionally substituted by one or more halogen atoms; c) a straight or branched alkyl-cycloalkyl or cycloalkylalkyl group substituted by one or more carboxylic groups (—COOH) and optionally substituted by one or more halogen atoms. Formula (I).

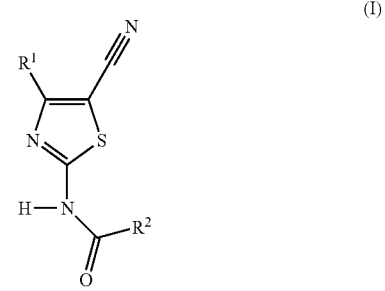

(I)

10 Claims, No Drawings

COMPOUNDS AS ADENOSINE $A_1$ RECEPTOR ANTAGONISTS

FIELD OF THE INVENTION

The present invention relates to new antagonists of adenosine receptors, in particular antagonists of the $A_1$ adenosine receptor subtype, the use of said compounds in the treatment of diseases susceptible of being ameliorated by antagonism of adenosine receptors, in particular in the treatment of cardiovascular, renal and respiratory disorders which are known to be improved by the use of antagonists of the $A_1$ adenosine receptors, more specifically disorders such as congestive heart failure, renal failure, hypertension intradialytic hypotension, ischemia, supraventricular arrhythmias, myocardial reperfusion injury, asthma, COPD and allergic rhinitis, and to pharmaceutical compositions comprising said compounds.

BACKGROUND OF THE INVENTION

The effects of adenosine are mediated through at least four specific cell membrane receptors so far identified and classified as receptors $A_1$, $A_{2A}$, $A_{2B}$ and $A_3$ belonging to the G protein-coupled receptor family. The $A_1$ and $A_3$ receptors down-regulate cellular cAMP levels through their coupling to G proteins, which inhibit adenylate cyclase. In contrast, $A_{2A}$ and $A_{2B}$ receptors couple to G proteins that activate adenylate cyclase and increase intracellular levels of cAMP. Through these receptors, adenosine regulates a wide range of physiological functions.

Thus, in the cardiovascular system the activation of the $A_1$ receptor protects cardiac tissue from the effects of ischemia and hypoxia (Norton G R et al. *Am J Physiol.* 1999; 276(2 Pt 2):H341-9; Auchampach J A, Bolli R. *Am J Physiol.* 1999; 276(3 Pt 2):H1113-6). The potential of A1 antagonists for the treatment of congestive hart failure is well documented in the literature (Jacobson K, Gao Z, *Nature Rev. Drug. Disc.* 2006; 5, 247-264) and also clinically validated by the positive results of phase II clinical trials with the compounds BG-9719 (Gottlieb S S et al, *Circulation,* 2002, 105, 1349-1353; Biogen idec, Website), BG-9928 (Greenberg B H et al, *Circulation,* 2003, 108, Abs 1602) and KW-3902 (Coletta A et al, *Eur. J. Heart Failure,* 2006, 8, 547-49; Novacardia, Website 2006). In the kidney, adenosine exerts a biphasic action, inducing vasodilatation at high concentrations and vasoconstriction at low concentrations. Thus, adenosine plays a role in the pathogenesis of some forms of acute renal failure that may be ameliorated by $A_1$ receptor antagonists (Costello-Boerrigter L C, et al. *Med Clin North Am.* 2003 March; 87(2): 475-91; Gottlieb S S., *Drugs.* 2001; 61(10): 1387-93). Recently the potential of A1 antagonists for the treatment of intradialytic hypotension has been demonstrated in clinical trials (E. Imai; M. Fuji, et al. *Kydney International,* 2006, 69, 877-883).

Moreover, the novel, potent and selective adenosine A1 receptor antagonist FR194921 exerts both cognitive-enhancing and anxiolytic activity, suggesting the therapeutic potential of such compounds for dementia and anxiety disorders (Maemoto T; Tada M, *J. Pharmacol. Sci.,* 2004, 96, 42-52).

A recent report revealed a strong expression of the adenosine A1 receptor located predominantly to the bronchial epithelium and bronchial smooth muscle. The sensitivity of asthmatics to inhaled adenosine coupled with increased adenosine A1 receptor expression implicates a role for these receptors in the pathophysiology of asthma and other respiratory diseases (Page C, *Eur Respir J,* 2007, 31(2):311-9).

Some derivatives of the 2-amino 1,3 thiazole are known as adenosine receptor antagonists (Moro S, et al. *Med. Res. Rev.,* 26, 131-159). Some patent applications claimed selective the $A_{2b}$ and $A_3$ (WO9964418, WO0242298, WO05063743) and selective $A_{2a}$ (WO06032273) receptor antagonists based on 2-amino-1,3 thiazole derivatives. One report (Ijzerman P, et al. *J. Med. Chem.* 2001, 44, 749-762) described selective A1 antagonists based on these structures, but the potency and selectivity published were modest, and the results were obtained using the rat instead the human adenosine receptors.

SUMMARY OF THE INVENTION

It has now been surprisingly found that new derivatives of the 5-cyano-2-amino-1,3 thiazole are potent and selective $A_1$ adenosine receptor antagonists, and can therefore be used in the treatment or prevention of diseases susceptible to amelioration by antagonism of the adenosine $A_1$ receptor. It has been further found that the introduction of a cyano group at position 5 of the thiazole ring plays an essential role in the activity of the compounds claimed in the present invention against the adenosine $A_1$ receptor, as can be demonstrated in the following example:

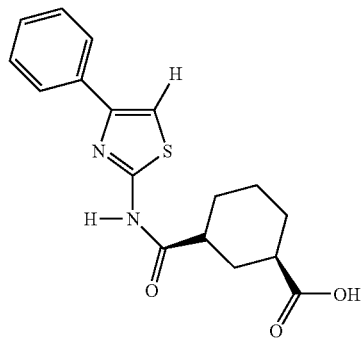

Inhibition constant (Ki) against
the $A_1$ adenosine receptor > 1 μM

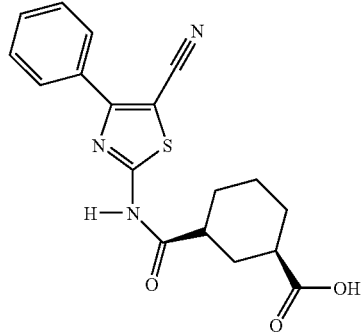

Inhibition constant (Ki) against
the $A_1$ adenosine receptor = 17 nM
(Example 8 of the present application)

Further objectives of the present invention are to provide a method for preparing said compounds; pharmaceutical compositions comprising an effective amount of said compounds; the use of the compounds in the manufacture of a medicament for the treatment of pathological conditions or diseases susceptible of being improved by antagonism of an adenosine receptor, in particular by antagonism of the $A_1$ adenosine receptor; methods of treatment of pathological conditions or diseases susceptible to amelioration by antagonism of an adenosine receptor, in particular by antagonism of the $A_1$ adenosine receptor comprising the administration of the compounds of the invention to a subject in need of treatment and combinations of said compounds with one or more of the following drugs:

(a) angiotensin converting enzyme inhibitors (ACE-inhibitors) (b) angiotensin receptor antagonists (ARB), (c) statins, (d) beta blockers, (e) calcium antagonists and (f) diuretics, (g) leukotriene antagonists, (h) corticosteroids, (i) aldosterone antagonists, (j) histamine antagonists, (k) CRTh2 antagonists, (l) renin inhibitors, (m) vasopressin antagonists

DETAILED DESCRIPTION OF THE INVENTION

Thus, the present invention is directed to 2-amino-5-cyano-1,3-thiazole derivatives of formula (I)

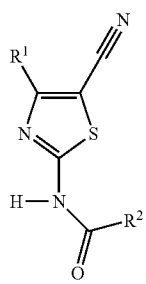

(I)

Wherein:
R$^1$ represents and aryl or heteroaryl group optionally substituted by one or more substituents selected from the group consisting of halogen atoms, straight or branched, optionally substituted lower alkyl, cycloalkyl, hydroxy, straight or branched, optionally substituted lower alkoxy, cyano, —CO$_2$R', wherein R' represents a hydrogen atom or a straight or branched, optionally substituted lower alkyl group;
R$^2$ represents a group selected from:
a) a straight or branched lower alkyl group substituted by one or more carboxylic groups (—COOH) and optionally substituted by one or more halogen atoms
b) a straight or branched cycloalkyl group substituted by one or more carboxylic groups (—COOH) and optionally substituted by one or more halogen atoms
c) a straight or branched alkylcycloalkyl or cycloalkylalkyl group substituted by one or more carboxylic groups (—COOH) and optionally substituted by one or more halogen atoms Other aspects of the present invention are: a) pharmaceutical compositions comprising an effective amount of said compounds, b) the use of said compounds in the manufacture of a medicament for the treatment of diseases susceptible of being improved by antagonism of an adenosine receptor, in particular by antagonism of the A$_1$ adenosine receptor; c) methods of treatment of diseases susceptible to amelioration by antagonism of an adenosine receptor, in particular by antagonism of the A$_1$ adenosine receptor and d) methods comprise the administration of the compounds of the invention to a subject in need of treatment and combinations of said compounds with one or more of the following drugs: (a) angiotensin converting enzyme inhibitors (ACE-inhibitors) (b) angiotensin receptor antagonists (ARB), (c) statins, (d) beta blockers, (e) calcium antagonists and (f) diuretics, (g) leukotriene antagonists, (h) corticosteroids, (i) aldosterone antagonists, (j) histamine antagonists, (k) CRTh2 antagonists, (l) renin inhibitors, (m) vasopressin antagonists.

As used herein the term lower alkyl embraces optionally substituted, linear or branched radicals having 1 to 8, preferably 1 to 6 and more preferably 1 to 4 carbon atoms.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term lower alkoxy embraces optionally substituted, linear or branched oxy-containing radicals each having alkyl portions of 1 to 8, preferably 1 to 6 and more preferably 1 to 4 carbon atoms.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term aryl group embraces typically a $C_5$-$C_{14}$ monocyclic or polycyclic aryl radical such as phenyl or naphthyl, anthranyl or phenanthryl. Phenyl is preferred. When an aryl radical carries 2 or more substituents, the substituents may be the same or different.

As used herein, the term heteroaryl group embraces typically a 5- to 14-membered ring system comprising at least one heteroaromatic ring and containing at least one heteroatom selected from O, S and N. A heteroaryl radical may be a single ring or two or more fused rings wherein at least one ring contains a heteroatom.

Examples include pyridyl, pyrazinyl, pyrimidinyl, pyridazinyl, furyl, oxadiazolyl, oxazolyl, imidazolyl, thiazolyl, thiadiazolyl, thienyl, pyrrolyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl and pyrazolyl radicals. The preferred radicals are thienyl and furyl optionally substituted.

When a heteroaryl radical carries 2 or more substituents, the substituents may be the same or different.

As used herein, the term cycloalkyl embraces saturated optionally substituted carbocyclic radicals and, unless otherwise specified, a cycloalkyl radical typically has from 3 to 7 carbon atoms.

Examples include cyclopropyl, cyclobutyl, cyclopentyl, cyclohexyl and cycloheptyl. It is preferably cyclopropyl, cyclopentyl or cyclohexyl. When a cycloalkyl radical carries 2 or more substituents, the substituents may be the same or different.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Preferred salts according to the invention are alkali metal salts as sodium or potassium salts.

According to one embodiment of the present invention in the compounds of formula (I), $R^1$ represents an aryl or heteroaryl group selected from the group consisting of phenyl, furyl, thienyl, 1,3-thiazolyl, oxazolyl, pyrazinyl, pyrazolyl, pyridazinyl, imidazolyl, triazolyl, pyrimidinyl and pyridyl groups which are optionally substituted by one or more substituents.

According to a preferred embodiment of the present invention in the compounds of formula (I), $R^1$ represents a monocyclic aryl or heteroaryl group selected from the group consisting of phenyl, thienyl or furyl groups which are optionally substituted by one or more substituents.

Particular individual compounds of the invention include:
5-(5-cyano-4-phenyl-1,3-thiazol-2-ylcarbamoyl)cyclohexane-1,3-dicarboxylic acid
4-(5-cyano-4-phenyl-1,3-thiazol-2-ylcarbamoyl)-4-methylpentanoic acid
4-(5-cyano-4-phenyl-1,3-thiazol-2-ylcarbamoyl)butanoic acid
(1R,3S)-3-(5-cyano-4-phenyl-1,3-thiazol-2-ylcarbamoyl)cyclopentane carboxylic acid
3-(5-cyano-4-phenyl-1,3-thiazol-2-ylcarbamoyl)cyclopentane carboxylic acid
cis-2-(5-cyano-4-phenyl-1,3-thiazol-2-ylcarbamoyl)cyclohexane carboxylic acid
trans-2-(5-cyano-4-phenyl-1,3-thiazol-2-ylcarbamoyl)cyclohexane carboxylic acid
cis-3-(5-cyano-4-phenyl-1,3-thiazol-2-ylcarbamoyl)cyclohexane carboxylic acid
trans-3-(5-cyano-4-phenyl-1,3-thiazol-2-ylcarbamoyl)cyclohexane carboxylic acid
cis-4-(5-cyano-4-phenyl-1,3-thiazol-2-ylcarbamoyl)cyclohexane carboxylic acid
trans-4-(5-cyano-4-phenyl-1,3-thiazol-2-ylcarbamoyl)cyclohexane carboxylic acid
4-(5-cyano-4-phenyl-1,3-thiazol-2-ylcarbamoyl)pentanoic acid
(R)-4-(5-cyano-4-phenyl-1,3-thiazol-2-ylcarbamoyl)pentanoic acid
(S)-4-(5-cyano-4-phenyl-1,3-thiazol-2-ylcarbamoyl)pentanoic acid
3-(5-cyano-4-phenyl-1,3-thiazol-2-ylcarbamoyl)-3-methylbutanoic acid
3-(5-cyano-4-phenyl-1,3-thiazol-2-ylcarbamoyl)butanoic acid
(R)-3-(5-cyano-4-phenyl-1,3-thiazol-2-ylcarbamoyl)butanoic acid
(S)-3-(5-cyano-4-phenyl-1,3-thiazol-2-ylcarbamoyl)butanoic acid
3-(5-cyano-4-phenyl-1,3-thiazol-2-ylcarbamoyl)cyclohexanecarboxylic acid
4-(5-cyano-4-phenyl-1,3-thiazol-2-ylcarbamoyl)cyclohexanecarboxylic acid
4-(5-cyano-4-phenyl-1,3-thiazol-2-ylcarbamoyl)bicyclo[2.2.2]octane-1-carboxylic acid
4-(5-cyano-4-phenyl-1,3-thiazol-2-ylcarbamoyl)-1,4-dimethyl cyclohexanecarboxylic acid
4-(5-cyano-4-phenyl-1,3-thiazol-2-ylcarbamoyl)-3-methylbutanoic acid
3-[5-cyano-4-(3-methylphenyl)-1,3-thiazol-2-ylcarbamoyl]cyclohexane carboxylic acid
4-[4-(2-chlorophenyl)-5-cyano-1,3-thiazol-2-ylcarbamoyl]-4-methylpentanoic acid
3-[4-(2-chlorophenyl)-5-cyano-1,3-thiazol-2-ylcarbamoyl]cyclohexane carboxylic acid
4-[4-(2-chlorophenyl)-5-cyano-1,3-thiazol-2-ylcarbamoyl]cyclohexane carboxylic acid
3-[4-(2-chlorophenyl)-5-cyano-1,3-thiazol-2-ylcarbamoyl]-3-methylbutanoic acid
4-[4-(3-chlorophenyl)-5-cyano-1,3-thiazol-2-ylcarbamoyl]-4-methylpentanoic acid
4-[4-(3-chlorophenyl)-5-cyano-1,3-thiazol-2-ylcarbamoyl]butanoic acid
cis-3-[4-(3-chlorophenyl)-5-cyano-1,3-thiazol-2-ylcarbamoyl]cyclopentanecarboxylic acid
trans-3-[4-(3-chlorophenyl)-5-cyano-1,3-thiazol-2-ylcarbamoyl]cyclopentanecarboxylic acid
cis-2-[4-(3-chlorophenyl)-5-cyano-1,3-thiazol-2-ylcarbamoyl]cyclohexanecarboxylic acid
trans-2-[4-(3-chlorophenyl)-5-cyano-1,3-thiazol-2-ylcarbamoyl]cyclohexane carboxylic acid
cis-3-[4-(3-chlorophenyl)-5-cyano-1,3-thiazol-2-ylcarbamoyl]cyclohexanecarboxylic acid
trans-3-[4-(3-chlorophenyl)-5-cyano-1,3-thiazol-2-ylcarbamoyl]cyclohexane carboxylic acid
cis-4-[4-(3-chlorophenyl)-5-cyano-1,3-thiazol-2-ylcarbamoyl]cyclohexane carboxylic acid
trans-4-[4-(3-chlorophenyl)-5-cyano-1,3-thiazol-2-ylcarbamoyl]cyclohexane carboxylic acid
4-[4-(3-chlorophenyl)-5-cyano-1,3-thiazol-2-ylcarbamoyl]pentanoic acid
(R)-4-[4-(3-chlorophenyl)-5-cyano-1,3-thiazol-2-ylcarbamoyl]pentanoic acid
(S)-4-[4-(3-chlorophenyl)-5-cyano-1,3-thiazol-2-ylcarbamoyl]pentanoic acid
3-[4-(3-chlorophenyl)-5-cyano-1,3-thiazol-2-ylcarbamoyl]-3-methylbutanoic acid
3-[4-(3-chlorophenyl)-5-cyano-1,3-thiazol-2-ylcarbamoyl]butanoic acid
(R)-3-[4-(3-chlorophenyl)-5-cyano-1,3-thiazol-2-ylcarbamoyl]butanoic acid
(S)-3-[4-(3-chlorophenyl)-5-cyano-1,3-thiazol-2-ylcarbamoyl]butanoic acid
3-[4-(3-chlorophenyl)-5-cyano-1,3-thiazol-2-ylcarbamoyl]cyclohexane carboxylic acid
4-[4-(3-chlorophenyl)-5-cyano-1,3-thiazol-2-ylcarbamoyl]cyclohexane carboxylic acid
4-[4-(3-chlorophenyl)-5-cyano-1,3-thiazol-2-ylcarbamoyl]bicyclo[2.2.2]octane-1-carboxylic acid
4-[5-cyano-4-(2-fluorophenyl)-1,3-thiazol-2-ylcarbamoyl]-4-methylpentanoic acid
4-[5-cyano-4-(2-fluorophenyl)-1,3-thiazol-2-ylcarbamoyl]butanoic acid
4-[5-cyano-4-(2-fluorophenyl)-1,3-thiazol-2-ylcarbamoyl]-3-methylbutanoic acid
cis-3-[5-cyano-4-(2-fluorophenyl)-1,3-thiazol-2-ylcarbamoyl]cyclopentanecarboxylic acid
trans-3-[5-cyano-4-(2-fluorophenyl)-1,3-thiazol-2-ylcarbamoyl]cyclopentane carboxylic acid cis-2-[5-cyano-4-(2-fluorophenyl)-1,3-thiazol-2-ylcarbamoyl]cyclohexanecarboxylic acid
trans-2-[5-cyano-4-(2-fluorophenyl)-1,3-thiazol-2-ylcarbamoyl]cyclohexane carboxylic acid
cis-3-[5-cyano-4-(2-fluorophenyl)-1,3-thiazol-2-ylcarbamoyl]cyclohexanecarboxylic acid
trans-3-[5-cyano-4-(2-fluorophenyl)-1,3-thiazol-2-ylcarbamoyl]cyclohexane carboxylic acid
cis-4-[5-cyano-4-(2-fluorophenyl)-1,3-thiazol-2-ylcarbamoyl]cyclohexanecarboxylic acid
trans-4-[5-cyano-4-(2-fluorophenyl)-1,3-thiazol-2-ylcarbamoyl]cyclohexane carboxylic acid
4-[5-cyano-4-(2-fluorophenyl)-1,3-thiazol-2-ylcarbamoyl]pentanoic acid
(R)-4-[5-cyano-4-(2-fluorophenyl)-1,3-thiazol-2-ylcarbamoyl]pentanoic acid
(S)-4-[5-cyano-4-(2-fluorophenyl)-1,3-thiazol-2-ylcarbamoyl]pentanoic acid
3-[5-cyano-4-(2-fluorophenyl)-1,3-thiazol-2-ylcarbamoyl]-3-methylbutanoic acid
3-[5-cyano-4-(2-fluorophenyl)-1,3-thiazol-2-ylcarbamoyl]butanoic acid
(R)-3-[5-cyano-4-(2-fluorophenyl)-1,3-thiazol-2-ylcarbamoyl]butanoic acid
(S)-3-[5-cyano-4-(2-fluorophenyl)-1,3-thiazol-2-ylcarbamoyl]butanoic acid
3-[5-cyano-4-(2-fluorophenyl)-1,3-thiazol-2-ylcarbamoyl]cyclohexane carboxylic acid
4-[5-cyano-4-(2-fluorophenyl)-1,3-thiazol-2-ylcarbamoyl]cyclohexane carboxylic acid
4-[5-cyano-4-(2-fluorophenyl)-1,3-thiazol-2-ylcarbamoyl]bicyclo[2.2.2]octane-1-carboxylic acid
4-[5-cyano-4-(3-fluorophenyl)-1,3-thiazol-2-ylcarbamoyl]-4-methylpentanoic acid
4-[5-cyano-4-(3-fluorophenyl)-1,3-thiazol-2-ylcarbamoyl]butanoic acid
4-[5-cyano-4-(3-fluorophenyl)-1,3-thiazol-2-ylcarbamoyl]-3-methylbutanoic acid
cis-3-[5-cyano-4-(3-fluorophenyl)-1,3-thiazol-2-ylcarbamoyl]cyclopentanecarboxylic acid
trans-3-[5-cyano-4-(3-fluorophenyl)-1,3-thiazol-2-ylcarbamoyl]cyclopentane carboxylic acid
cis-2-[5-cyano-4-(3-fluorophenyl)-1,3-thiazol-2-ylcarbamoyl]cyclohexanecarboxylic acid
trans-2-[5-cyano-4-(3-fluorophenyl)-1,3-thiazol-2-ylcarbamoyl]cyclohexane carboxylic acid
cis-3-[5-cyano-4-(3-fluorophenyl)-1,3-thiazol-2-ylcarbamoyl]cyclohexanecarboxylic acid
trans-3-[5-cyano-4-(3-fluorophenyl)-1,3-thiazol-2-ylcarbamoyl]cyclohexane carboxylic acid
cis-4-[5-cyano-4-(3-fluorophenyl)-1,3-thiazol-2-ylcarbamoyl]cyclohexanecarboxylic acid
trans-4-[5-cyano-4-(3-fluorophenyl)-1,3-thiazol-2-ylcarbamoyl]cyclohexane carboxylic acid
4-[5-cyano-4-(3-fluorophenyl)-1,3-thiazol-2-ylcarbamoyl]pentanoic acid
(R)-4-[5-cyano-4-(3-fluorophenyl)-1,3-thiazol-2-ylcarbamoyl]pentanoic acid
(S)-4-[5-cyano-4-(3-fluorophenyl)-1,3-thiazol-2-ylcarbamoyl]pentanoic acid
3-[5-cyano-4-(3-fluorophenyl)-1,3-thiazol-2-ylcarbamoyl]-3-methylbutanoic acid
3-[5-cyano-4-(3-fluorophenyl)-1,3-thiazol-2-ylcarbamoyl]butanoic acid
(R)-3-[5-cyano-4-(3-fluorophenyl)-1,3-thiazol-2-ylcarbamoyl]butanoic acid
(S)-3-[5-cyano-4-(3-fluorophenyl)-1,3-thiazol-2-ylcarbamoyl]butanoic acid
3-[5-cyano-4-(3-fluorophenyl)-1,3-thiazol-2-ylcarbamoyl]cyclohexane carboxylic acid
4-[5-cyano-4-(3-fluorophenyl)-1,3-thiazol-2-ylcarbamoyl]cyclohexane carboxylic acid
4-[5-cyano-4-(3-fluorophenyl)-1,3-thiazol-2-ylcarbamoyl]bicyclo[2.2.2]octane-1-carboxylic acid
4-[5-cyano-4-(4-fluorophenyl)-1,3-thiazol-2-ylcarbamoyl]-4-methylpentanoic acid
4-[5-cyano-4-(4-fluorophenyl)-1,3-thiazol-2-ylcarbamoyl]butanoic acid
4-[5-cyano-4-(4-fluorophenyl)-1,3-thiazol-2-ylcarbamoyl]-3-methylbutanoic acid
cis-3-[5-cyano-4-(4-fluorophenyl)-1,3-thiazol-2-ylcarbamoyl]cyclopentanecarboxylic acid
trans-3-[5-cyano-4-(4-fluorophenyl)-1,3-thiazol-2-ylcarbamoyl]cyclopentane carboxylic acid
cis-2-[5-cyano-4-(4-fluorophenyl)-1,3-thiazol-2-ylcarbamoyl]cyclohexanecarboxylic acid
trans-2-[5-cyano-4-(4-fluorophenyl)-1,3-thiazol-2-ylcarbamoyl]cyclohexane carboxylic acid
cis-3-[5-cyano-4-(4-fluorophenyl)-1,3-thiazol-2-ylcarbamoyl]cyclohexanecarboxylic acid
trans-3-[5-cyano-4-(4-fluorophenyl)-1,3-thiazol-2-ylcarbamoyl]cyclohexane carboxylic acid
cis-4-[5-cyano-4-(4-fluorophenyl)-1,3-thiazol-2-ylcarbamoyl]cyclohexanecarboxylic acid
trans-4-[5-cyano-4-(4-fluorophenyl)-1,3-thiazol-2-ylcarbamoyl]cyclohexane carboxylic acid
4-[5-cyano-4-(4-fluorophenyl)-1,3-thiazol-2-ylcarbamoyl]pentanoic acid
(R)-4-[5-cyano-4-(4-fluorophenyl)-1,3-thiazol-2-ylcarbamoyl]pentanoic acid
(S)-4-[5-cyano-4-(4-fluorophenyl)-1,3-thiazol-2-ylcarbamoyl]pentanoic acid
3-[5-cyano-4-(4-fluorophenyl)-1,3-thiazol-2-ylcarbamoyl]-3-methylbutanoic acid
3-[5-cyano-4-(4-fluorophenyl)-1,3-thiazol-2-ylcarbamoyl]butanoic acid
(R)-3-[5-cyano-4-(4-fluorophenyl)-1,3-thiazol-2-ylcarbamoyl]butanoic acid
(S)-3-[5-cyano-4-(4-fluorophenyl)-1,3-thiazol-2-ylcarbamoyl]butanoic acid
3-[5-cyano-4-(4-fluorophenyl)-1,3-thiazol-2-ylcarbamoyl]cyclohexane carboxylic acid
4-[5-cyano-4-(4-fluorophenyl)-1,3-thiazol-2-ylcarbamoyl]cyclohexane carboxylic acid
4-[5-cyano-4-(4-fluorophenyl)-1,3-thiazol-2-ylcarbamoyl]bicyclo[2.2.2]octane-1-carboxylic acid
4-[5-cyano-4-(3,4-difluorophenyl)-1,3-thiazol-2-ylcarbamoyl]-4-methylpentanoic acid
3-[5-cyano-4-(3,4-difluorophenyl)-1,3-thiazol-2-ylcarbamoyl]cyclohexanecarboxylic acid
4-[5-cyano-4-(3,4-difluorophenyl)-1,3-thiazol-2-ylcarbamoyl]cyclohexanecarboxylic acid
4-[5-cyano-4-(3,5-difluorophenyl)-1,3-thiazol-2-ylcarbamoyl]-4-methylpentanoic acid
3-[5-cyano-4-(3,5-difluorophenyl)-1,3-thiazol-2-ylcarbamoyl]cyclohexanecarboxylic acid
4-[5-cyano-4-(3,5-difluorophenyl)-1,3-thiazol-2-ylcarbamoyl]cyclohexanecarboxylic acid
3-[5-cyano-4-(3-trifluoromethylphenyl)-1,3-thiazol-2-ylcarbamoyl]cyclohexane carboxylic acid
4-[5-cyano-4-(3-trifluoromethylphenyl)-1,3-thiazol-2-ylcarbamoyl]cyclohexane carboxylic acid
4-[5-cyano-4-(3-trifluoromethylphenyl)-1,3-thiazol-2-ylcarbamoyl]bicyclo[2.2.2]octane-1-carboxylic acid
3-[5-cyano-4-(pyridin-4-yl)-1,3-thiazol-2-ylcarbamoyl]cyclohexane carboxylic acid
4-[5-cyano-4-(pyridin-4-yl)-1,3-thiazol-2-ylcarbamoyl]cyclohexane carboxylic acid
4-[5-cyano-4-(pyridin-4-yl)-1,3-thiazol-2-ylcarbamoyl]bicyclo[2.2.2]octane-1-carboxylic acid 4-[5-cyano-4-(pyridin-3-yl)-1,3-thiazol-2-ylcarbamoyl]-4-methyl pentanoic acid
3-[5-Cyano-4-(pyridin-3-yl)-1,3-thiazol-2-ylcarbamoyl]cyclohexane carboxylic acid
4-[5-Cyano-4-(pyridin-3-yl)-1,3-thiazol-2-ylcarbamoyl]cyclohexane carboxylic acid
4-[5-cyano-4-(pyridin-2-yl)-1,3-thiazol-2-ylcarbamoyl]-4-methyl pentanoic acid
3-[5-Cyano-4-(pyridin-2-yl)-1,3-thiazol-2-ylcarbamoyl]cyclohexane carboxylic acid
4-[5-Cyano-4-(pyridin-2-yl)-1,3-thiazol-2-ylcarbamoyl]cyclohexane carboxylic acid
4-[5-cyano-4-(furan-2-yl)-1,3-thiazol-2-ylcarbamoyl]-4-methyl pentanoic acid
3-[5-cyano-4-(furan-2-yl)-1,3-thiazol-2-ylcarbamoyl]cyclohexane carboxylic acid
4-[5-cyano-4-(furan-2-yl)-1,3-thiazol-2-ylcarbamoyl]cyclohexane carboxylic acid
4-[5-cyano-4-(4-methylfuran-3-yl)-1,3-thiazol-2-ylcarbamoyl]-4-methylpentanoic acid
3-[5-cyano-4-(4-methylfuran-3-yl)-1,3-thiazol-2-ylcarbamoyl]cyclohexanecarboxylic acid
4-[5-cyano-4-(4-methylfuran-3-yl)-1,3-thiazol-2-ylcarbamoyl]cyclohexanecarboxylic acid The compounds of the present invention can be prepared by one of the processes described below.

drofuran, dioxane or diethyl ether (Polivka, Z, et al., *Collect. Czech. Chem. Commun.*, 1984, 49, 621-36).

Alternatively, the compounds of formula (III) can be obtained by a two step procedure (Scheme 1) starting from commercially available methyl ketones of formula (V), wherein $R^1$ was defined before. In the first step, compounds of formula (V) are brominated or iodinated using N-Bromsuccinimide or N-Iodsuccinimide under standard conditions obtaining bromo or iodo ketones of formula (VI). The halogen atom of these haloketones of formula (VI) can be substituted by a cyano group using sodium or potassium cyanide leading to the desired cyano ketones of formula (III) (Reidlinger, C, et al., *Monatsh. Chem.*, 1998, 129: 1207-12; Compton, V, et al. *J. Chem. Soc. Perkin Trans.* 1, 1992, 2029-32).

On the other hand, acylation of compounds of formula (VII) with cyanoacetic acid or an activated derivative under Friedel-Craft conditions constitutes an alternative method to synthesize the intermediates cyanoketones of formula (III) (I. G. Farbenindustrie DE 544886).

The 2-amino-5-cyano-1,3-thiazole derivatives of formula (VIII), wherein $R^1$ is an aryl or heteroaryl group optionally substituted as defined above, can be obtained by reaction of the cyanoketones of formula (III) with iodine and thiourea in a solvent like pyridine or dimethylformamide at a temperature between 80° C. and 120° C. (Scheme 2).

Scheme 1

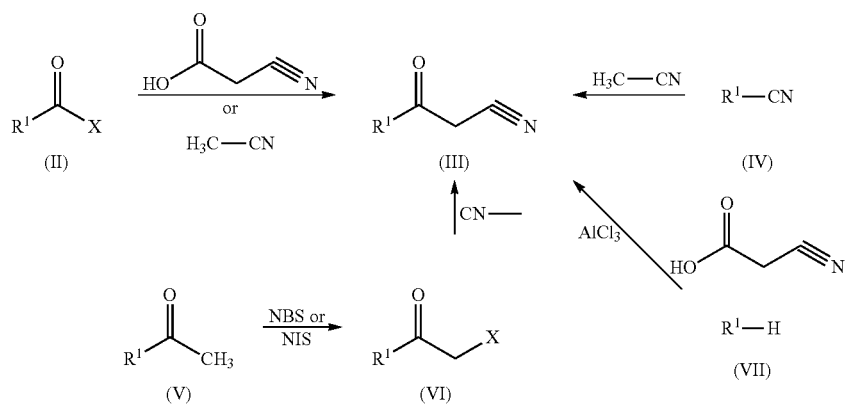

The cyanoketones of formula (III), wherein $R^1$ is an aryl or heteroaryl group optionally substituted as defined above can be obtained by reaction of a carboxylic acid derivative of formula (II), wherein X is a good leaving group like for example an halogen or O-alkyl, with acetonitrile or cyanoacetic acid in the presence of a base. The base selected for this reaction could be butyl lithium in an aprotic solvent like diethyl ether or tetrahydrofuran (Turner J., et al. *Synthesis.* 1983, 308-9), or sodium hydride, sodium methoxide or potassium tert-butoxide, in a solvent like toluene, diethyl ether, tetrahydrofuran, dioxane, ethanol or methanol at a temperature between 40° C. and 120° C. (Dorsch M, et al. *J. Am. Chem. Soc.* 1932, 54, 2960-63; Turner J., et al. *J. Org. Chem.* 1989; 54, 4229-31).

The cyanoketones of formula (III), wherein $R^1$ is an aryl or heteroaryl group optionally substituted as defined above can also be obtained by reaction of aromatic nitriles of formula (IV) with acetonitrile in the presence of a strong base as sodium hydride, sodium methoxide potassium tert-butoxide or lithium bis(trimethylsilyl)amide in a solvent like tetrahydrofuran, dioxane or diethyl ether Scheme 2

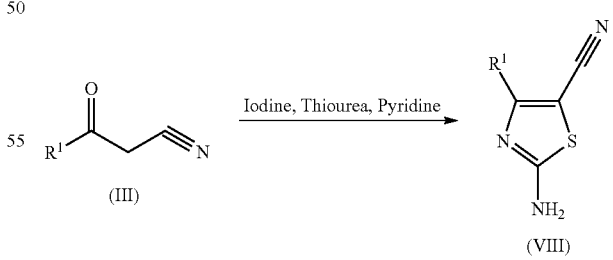

The compounds of formula (VIII) can be acylated using either a carboxylic acid chloride derivative of formula (IX) or a carboxylic acid anhydride of formula (X), where $R^3$ was defined above, giving the amide derivatives of formula (XI) which are particular cases of the compounds claimed by the present invention.

Scheme 3

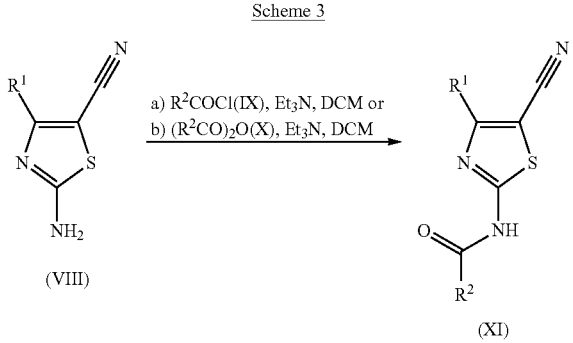

Pharmacological Activity

Adenosine Receptor Subtype Competition Radioligand Binding Assay

Human membranes from recombinant adenosine receptors were purchased from Receptor Biology, Inc. (USA)

Competition assays were carried out by incubation of membranes from $hA_1$ receptors transfected to CHO cells, [$^3$H]-DPCPX as radioligand, buffer (HEPES 20 mM (pH=7.4), 10 mM $MgCl_2$, 100 mM NaCl, 2 units/ml adenosine deaminase), and unlabelled ligand in a total volume of 0.2 ml for 90 min at 25° C. R-PIA was used to determinate non-specific binding. Filter over Schleicher & Schuell GF/52 filters (pre-soaked 0.5% polyethylenimine) in a Brandel cell harvester. Unbound radioligand was removed with HEPES 30 mM (3×250 µl), NaCl (100 mM) and $MgCl_2$ (10 mM).

Competition assays were carried out by incubation of membranes from $hA_{2a}$ receptors transfected to HEK293 cells, [$^3$H]ZM241385 as radioligand, buffer (50 mM Tris-HCl (pH=7.4), 10 mM $MgCl_2$, 1 mM EMA, 2 units/ml adenosine deaminase), and unlabelled ligand in a total volume of 0.2 ml for 90 min at 25° C. NECA was used to determinate non-specific binding. Filter over Schleicher & Schuell GF/52 filters (pre-soaked 0.5% polyethylenimine) in a Brandel cell harvester. Unbound radioligand was removed with 3×3 ml ice-cold 50 mM Tris-HCl (pH=7.4), 0.9% NaCl.

The compounds of the present invention have not shown any relevant affinity for the adenosine receptors $A_3$ and $A_{2b}$. The inhibition constants (Ki) of some compounds claimed by the present invention for the adenosine $A_1$ and $A_{2a}$ receptors are shown in Table 1:

TABLE 1

| COMPOUNDS | $A_1$ Antagonism (Ki nM) | $A_{2a}$ Antagonism (Ki nM) |
|---|---|---|
| Example 2: 4-(5-cyano-4-phenyl-1,3-thiazol-2-ylcarbamoyl)-4-methylpentanoic acid | 43 | >10000 |
| Example 5: 3-(5-cyano-4-phenyl-1,3-thiazol-2-ylcarbamoyl)cyclopentane carboxylic acid | 6.4 | 940 |
| Example 8: cis-3-(5-cyano-4-phenyl-1,3-thiazol-2-ylcarbamoyl)cyclohexane carboxylic acid | 17 | >1200 |
| Example 10: cis-4-(5-cyano-4-phenyl-1,3-thiazol-2-ylcarbamoyl)cyclohexane carboxylic acid | 7 | 1082 |
| Example 26: cis-3-[4-(2-chlorophenyl)-5-cyano-1,3-thiazol-2-ylcarbamoyl]cyclohexane carboxylic acid | 31 | 3670 |

TABLE 1-continued

| COMPOUNDS | $A_1$ Antagonism (Ki nM) | $A_{2a}$ Antagonism (Ki nM) |
|---|---|---|
| Example 36: trans-4-[4-(3-chlorophenyl)-5-cyano-1,3-thiazol-2-ylcarbamoyl]cyclohexanecarboxylic acid | 25 | 487 |
| Example 50: cis-3-[5-cyano-4-(2-fluorophenyl)-1,3-thiazol-2-ylcarbamoyl] cyclopentanecarboxylic acid | 16 | >1300 |
| Example 68: 4-[5-cyano-4-(3-fluorophenyl)-1,3-thiazol-2-ylcarbamoyl]-4-methylpentanoic acid | 51 | >4000 |
| Example 75: cis-3-[5-cyano-4-(3-fluorophenyl)-1,3-thiazol-2-ylcarbamoyl] cyclohexanecarboxylic acid | 14 | 1841 |
| Example 77: cis-4-[5-cyano-4-(3-fluorophenyl)-1,3-thiazol-2-ylcarbamoyl] cyclohexanecarboxylic acid | 6 | 776 |
| Example 114: 3-[5-cyano-4-(3,5-difluorophenyl)-1,3-thiazol-2-ylcarbamoyl] cyclohexanecarboxylic acid | 32 | >10000 |
| Example 126: 3-[5-Cyano-4-(pyridin-2-yl)-1,3-thiazol-2-ylcarbamoyl]cyclohexanecarboxylic acid | 1100 | >10000 |

It can be seen from Table 1 that the compounds of formula (I) are potent inhibitors of the $A_1$ adenosine receptor subtype and selective against the $A_{2a}$ adenosine receptor. The 2-amido-5-cyano-1,3-thiazole derivatives of the invention are useful in the treatment or prevention of diseases known to be susceptible to improvement by treatment with an antagonist of an adenosine receptor, in particular those susceptible to improvement by treatment with and antagonist of the $A_1$ adenosine receptor. Such diseases are, for example congestive heart failure, hypertension, ischemia, supraventricular arrhythmias, acute renal failure, myocardial reperfusion injury, intradialytic hypotension, dementia, anxiety disorders and respiratory diseases like asthma and allergic rhinitis.

Accordingly, the 2-amido-5-cyano-1,3-thiazole derivatives of the invention and pharmaceutically acceptable salts thereof, and pharmaceutical compositions comprising such compound and/or salts thereof, may be used in a method of treatment of disorders of the human body which comprises administering to a subject requiring such treatment an effective amount of 2-amido-5-cyano-1,3 thiazole derivative of the invention or a pharmaceutically acceptable salt thereof.

The present invention also provides pharmaceutical compositions which comprise, as an active ingredient, at least a 2-amino-5-cyano-1,3-thiazole derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The examples are given by way of illustration and do not limit the scope of the invention in any way.

The synthesis of the compounds of the invention is illustrated by the following Examples (1 to 136) including the preparation of the intermediates, which do not limit the scope of the invention in any way.

General. Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 µm) with the solvent system indicated. Spectroscopic data were recorded on a Varian Gemini 200 spectrometer, Varian Gemini 300 spectrometer, Varian (nova 400 spectrometer and Brucker DPX-250 spectrometer. Melting points were recorded on a Büchi 535 apparatus. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector. Semi-preparative purifications were carried out using a Symmetry C18 reverse phase column (100 Å, 5 µm, 19×100 mm, purchased from WATERS), and water/ammonium formiate (0.1%, pH=3) and acetonitrile/ammonium formiate (0.1%, pH=3) as mobile phase.

Intermediate 1

2-Amino-4-phenyl-1,3-thiazol-5-carbonitrile

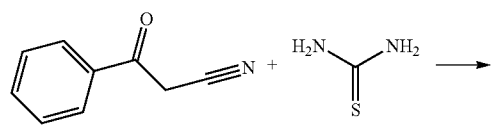

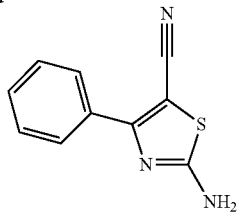

5 g (34.0 mmol) of 3-oxo-3-(3-fluorophenyl)-propanenitrile were dissolved in pyridine (30 ml) and thiourea (5 g, 68.0 mmol) and iodine (8.70 g, 34.40 mmol) were added successively. The solution was stirred at 100° C. for 12 h. The mixture was then cooled to room temperature and poured into ice-water (500 ml). The resulting solid was filtered, washed with water and recrystallized from ethanol to give 7.0 g (91%) of a yellow solid.

NMR (300 MHz, DMSO-$d_6$): δ=7.52 (m, 3H), 7.93 (d, 2H), 8.26 (s, 2H).

The following Intermediates have been synthesized using the procedure described for the Intermediate 1 starting from the corresponding ketonitriles.

Intermediate 2

2-Amino-4-(3-methylphenyl)-1,3-thiazol-5-carbonitrile

NMR (300 MHz, DMSO-$d_6$): δ=2.37 (s, 3H), 7.32 (d, 1H), 7.41 (t, 1H), 7.74 (m, 2H), 8.24 (s, 2H).

Intermediate 3

2-Amino-4-(2-chlorophenyl)-1,3-thiazol-5-carbonitrile

NMR (300 MHz, DMSO-$d_6$): δ=7.49 (m, 1H), 7.53 (m, 2H), 7.60 (m, 1H), 8.28 (s, 2H).

Intermediate 4

2-Amino-4-(3-chlorophenyl)-1,3-thiazol-5-carbonitrile

NMR (300 MHz, DMSO-$d_6$): δ=7.57 (d, 2H), 7.92 (m, 2H), 8.31 (s, 2H).

Intermediate 5

2-Amino-4-(2-fluorophenyl)-1,3-thiazol-5-carbonitrile

NMR (300 MHz, DMSO-$d_6$): δ=7.32 (dd, 1H), 7.38 (d, 1H), 7.54 (m, 1H), 7.65 (m, 1H), 8.24 (s, 2H).

Intermediate 6

2-Amino-4-(3-fluorophenyl)-1,3-thiazol-5-carbonitrile

NMR (300 MHz, DMSO-$d_6$): δ=7.35 (m, 1H), 7.59 (q, 1H), 7.65 (dd, 1H), 7.79 (dd, 1H), 8.31 (s, 2H).

Intermediate 7

2-Amino-4-(4-fluorophenyl)-1,3-thiazol-5-carbonitrile

NMR (300 MHz, DMSO-$d_6$): δ=7.32 (t, 2H), 7.96 (m, 2H), 8.30 (s, 2H).

Intermediate 8

2-Amino-4-(3,4-difluorophenyl)-1,3-thiazol-5-carbonitrile

NMR (300 MHz, DMSO-$d_6$): δ=7.63 (dd, 1H), 7.81 (dd, 1H), 7.87 (m, 1H), 8.32 (s, 2H).

Intermediate 9

2-Amino-4-(3,5-difluorophenyl)-1,3-thiazol-5-carbonitrile

NMR (300 MHz, DMSO-$d_6$): δ=7.45 (m, 1H), 7.57 (dd, 2H), 8.35 (s, 2H).

Intermediate 10

2-Amino-4-(2,5-difluorophenyl)-1,3-thiazol-5-carbonitrile

NMR (300 MHz, DMSO-$d_6$): δ=7.47 (m, 3H), 8.33 (s, 2H).

Intermediate 11

2-Amino-4-(3-trifluoromethylphenyl)-1,3-thiazol-5-carbonitrile

NMR (300 MHz, DMSO-$d_6$): δ=7.80 (t, 1H), 7.88 (d, 1H), 8.23 (m, 2H), 8.36 (s, 2H).

Intermediate 12

2-Amino-4-(pyridin-4-yl)-1,3-thiazol-5-carbonitrile

NMR (300 MHz, DMSO-$d_6$): δ=7.38 (d, 2H), 8.29 (s, 2H), 8.50 (d, 2H).

Intermediate 13

2-Amino-4-(pyridin-3-yl)-1,3-thiazol-5-carbonitrile

NMR (300 MHz, DMSO-$d_6$): δ=7.57 (m, 1H), 8.27 (d, 1H), 8.30 (s, 2H), 8.68 (d, 1H), 9.10 (s, 1H).

Intermediate 14

2-Amino-4-(pyridin-2-yl)-1,3-thiazol-5-carbonitrile

NMR (300 MHz, DMSO-$d_6$): δ=7.45 (m, 1H), 7.98 (m, 2H), 8.28 (s, 2H), 8.69 (m, 1H).

Intermediate 15

2-Amino-4-(furan-2-yl)-1,3-thiazol-5-carbonitrile

NMR (300 MHz, DMSO-$d_6$): δ=6.69 (dd, 1H), 6.93 (d, 1H), 7.91 (d, 1H), 8.24 (s, 2H).

Intermediate 16

2-Amino-4-(4-methylfuran-3-yl)-1,3-thiazol-5-carbonitrile

NMR (300 MHz, DMSO-$d_6$): δ=2.57 (s, 3H), 6.88 (d, 1H), 7.65 (d, 1H), 8.17 (s, 2H).

Synthesis of the Carboxylic Acid Chlorides:

Not commercially available carboxylic acid chlorides have been synthesized from the corresponding carboxylic acids using standard procedures (Burdett, K. A., *Sintesis,* 1991, 441-42) as exemplified below:

1,3,5 Cyclohexanecarboxylic Acid Trichloride 0.5 g (2.3 mmol) 1,3,5 cyclohexane carboxylic acid have been dissolved in 1,2-dichloroethane (5 ml). To this solution benzyl triethyl ammonium chloride (0.001 g, 3 µmol) and thionyl chloride (0.562 ml, 7.7 mmol) was then added. The suspension has been stirred at 90° C. for 16 h. The solution was concentrated and the residue was used in the acylation reaction without further purification.

Synthesis of the Carboxylic Acid Anhydrides

3-oxa-bicyclo[3.3.1]nonane-2,4-dione (cis-1,3-cyclohexane Dicarboxylic Anhydride)

10 g (58.2 mmol) 1,3-cyclohexane dicarboxylic acid were suspended in acetic anhydride (40 ml) and refluxed during 5 h. The solution was then cooled to room temperature and the solvents were removed in vacuo. The residue was then dissolved in a mixture of heptane (20 ml) and toluene (20 ml) and the solution was cooled to 4° C. The precipitated solid was then collected by filtration and washed with pentane to give 5.9 g of the titled compound as white needles.

EXAMPLES

Derivatives of Intermediate 1

Example 1

5-(5-cyano-4-phenyl-1,3-thiazol-2-ylcarbamoyl) cyclohexane-1,3-dicarboxylic Acid

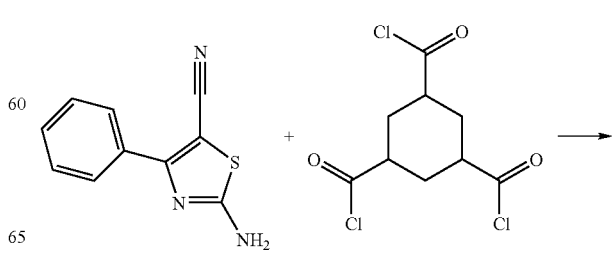

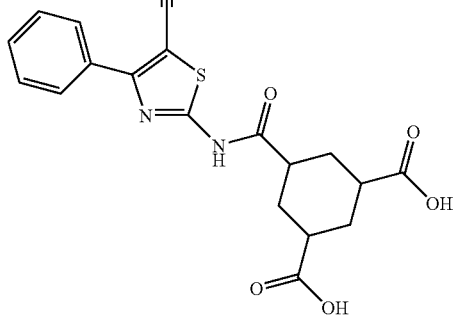

Intermediate 1 (200 mg, 1.0 mmol) was dissolved in dichloromethane (10 ml), and triethylamine (1 ml) and cyclohexane 1,3,5-tricarbonyl chloride (0.2 ml, 1.5 mmol) was added. The solution was stirred at room temperature for 12 h. The solvents were then evaporated. The residue was dissolved in methanol, a 4M sodium hydroxide solution (1 mL) was added and the mixture stirred at 60° C. for 12 h. The solution was poured into ice-water (50 ml). The resulting solution was washed with dichloromethane (2×15 ml). The water phase was brought to pH=3 using a cold 1M solution of hydrochloric acid. The precipitated solid was then filtered, washed with cold water and dried to give 290 mg (68%) of the desired compound as a pale yellow solid.

NMR (300 MHz, DMSO-$d_6$): δ=1.12 (m, 2H), 1.31 (m, 1H), 2.13 (m, 2H), 2.41 (m, 1H), 2.91 (m, 2H), 3.16 (m, 1H), 7.56 (m, 3H), 8.02 (m, 2H), 12.01 (s, 2H), 13.06 (s, 1H).

The following Examples have been synthesized using the procedure described for the Example 1 employing the corresponding intermediate and the carboxylic acid chloride or anhydride as starting materials.

Example 2

4-(5-cyano-4-phenyl-1,3-thiazol-2-ylcarbamoyl)-4-methylpentanoic Acid

NMR (300 MHz, DMSO-$d_6$): δ=1.26 (s, 6H), 1.95 (m, 2H), 2.13 (m, 2H), 7.56 (m, 3H), 8.02 (m, 2H), 12.17 (s, 1H), 12.87 (s, 1H).

Example 3

4-(5-cyano-4-phenyl-1,3-thiazol-2-ylcarbamoyl) butanoic Acid

NMR (300 MHz, DMSO-$d_6$): δ=1.85 (q, 2H), 2.30 (t, 2H), 2.58 (t, 2H), 7.57 (m, 3H), 8.01 (m, 2H), 12.15 (s, 1H), 13.08 (s, 1H).

Example 4

(1R,3S)-3-(5-cyano-4-phenyl-1,3-thiazol-2-ylcarbamoyl)cyclopentane Carboxylic Acid NMR (300 MHz, DMSO-$d_6$): δ=1.88 (m, 4H), 1.99 (m, 1H), 2.22 (m, 1H), 2.79 (m, 1H), 3.06 (m, 1H), 7.57 (m, 3H), 7.99 (m, 2H), 12.37 (s, 1H), 12.89 (s, 1H).

Example 5

3-(5-cyano-4-phenyl-1,3-thiazol-2-ylcarbamoyl) cyclopentane Carboxylic Acid

NMR (300 MHz, DMSO-$d_6$): δ=1.78 (m, 1H), 1.88 (m, 2H), 1.97 (m, 2H), 2.24 (m, 1H), 2.80 (m, 1H), 3.08 (m, 1H), 7.56 (m, 3H), 8.01 (m, 2H), 12.20 (s, 1H), 13.12 (s, 1H).

Example 6

Cis-2-(5-cyano-4-phenyl-1,3-thiazol-2-ylcarbamoyl) cyclohexane Carboxylic Acid

The compound has been synthesized using the anhydride as acylating agent.

NMR (300 MHz, DMSO-$d_6$): δ=1.37 (m, 3H), 1.64 (m, 1H), 1.76 (m, 2H), 1.92 (m, 1H), 2.07 (m, 1H), 2.80 (m, 1H), 3.12 (m, 1H), 7.56 (m, 3H), 8.01 (m, 2H), 12.40 (s, 1H), 12.93 (s, 1H).

Example 7 trans-2-(5-cyano-4-phenyl-1,3-thiazol-2-ylcarbamoyl)cyclohexane Carboxylic Acid

NMR (300 MHz, DMSO-$d_6$): δ=1.38 (m, 3H), 1.63 (m, 1H), 1.76 (m, 2H), 1.92 (m, 1H), 2.07 (m, 1H), 2.80 (m, 1H), 3.12 (m, 1H), 7.56 (m, 3H), 8.01 (m, 2H), 12.25 (s, 1H), 13.02 (s, 1H).

Example 8

Cis-3-(5-cyano-4-phenyl-1,3-thiazol-2-ylcarbamoyl) cyclohexane Carboxylic Acid

The compound has been synthesized using the anhydride as acylating agent.

NMR (300 MHz, DMSO-$d_6$): δ=1.31 (m, 3H), 1.50 (m, 1H), 1.90 (m, 3H), 2.09 (m, 1H), 2.28 (m, 1H), 2.61 (m, 1H), 7.56 (m, 3H), 8.01 (m, 2H), 12.18 (s, 1H), 13.07 (s, 1H).

Example 9 trans-3-(5-cyano-4-phenyl-1,3-thiazol-2-ylcarbamoyl)cyclohexane Carboxylic Acid

NMR (300 MHz, DMSO-$d_6$): δ=1.30 (m, 3H), 1.47 (m, 1H), 1.87 (m, 3H), 2.05 (m, 1H), 2.25 (m, 1H), 2.56 (m, 1H), 7.56 (m, 3H), 8.00 (m, 2H), 12.21 (s, 1H), 13.05 (s, 1H).

Example 10

Cis-4-(5-cyano-4-phenyl-1,3-thiazol-2-ylcarbamoyl) cyclohexane Carboxylic Acid

NMR (300 MHz, DMSO-$d_6$): δ=1.57 (m, 2H), 1.71 (m, 4), 1.96 (m, 2H), 2.55 (m, 1H), 2.67 (m, 1H), 7.56 (d, 3H), 8.01 (m, 2H), 12.15 (s, 1H), 12.95 (s, 1H).

Example 11 trans-4-(5-cyano-4-phenyl-1,3-thiazol-2-ylcarbamoyl)cyclohexane Carboxylic Acid

NMR (300 MHz, DMSO-$d_6$): δ=1.37 (m, 2H), 1.46 (m, 2), 1.97 (t, 4), 2.23 (t, 1H), 2.54 (t, 1H), 7.57 (d, 3H), 8.00 (m, 2H), 12.14 (s, 1H), 13.08 (s, 1H).

Example 12

4-(5-cyano-4-phenyl-1,3-thiazol-2-ylcarbamoyl)pentanoic Acid

NMR (300 MHz, DMSO-$d_6$): δ=1.17 (d, 3H), 1.72 (m, 1H), 1.88 (m, 1H), 2.23 (m, 2H), 2.74 (m, 1H), 7.57 (m, 3H), 8.00 (m, 2H), 12.17 (s, 1H), 13.12 (s, 1H).

Example 13

(R)-4-(5-cyano-4-phenyl-1,3-thiazol-2-ylcarbamoyl)pentanoic Acid

NMR (300 MHz, DMSO-$d_6$): δ=1.16 (d, 3H), 1.73 (m, 1H), 1.88 (m, 1H), 2.24 (m, 2H), 2.73 (m, 1H), 7.56 (m, 3H), 8.01 (m, 2H), 12.16 (s, 1H), 13.13 (s, 1H).

Example 14

(S)-4-(5-cyano-4-phenyl-1,3-thiazol-2-ylcarbamoyl)pentanoic Acid

NMR (300 MHz, DMSO-$d_6$): δ=1.17 (d, 3H), 1.71 (m, 1H), 1.88 (m, 1H), 2.22 (m, 2H), 2.74 (m, 1H), 7.56 (m, 3H), 8.00 (m, 2H), 12.17 (s, 1H), 13.11 (s, 1H).

Example 15

3-(5-cyano-4-phenyl-1,3-thiazol-2-ylcarbamoyl)-3-methylbutanoic Acid

NMR (300 MHz, DMSO-$d_6$): δ=1.23 (s, 6H), 2.78 (s, 2H), 7.56 (m, 3H), 8.01 (m, 2H), 12.53 (s, 1H), 12.99 (s, 1H).

Example 16

3-(5-cyano-4-phenyl-1,3-thiazol-2-ylcarbamoyl)butanoic Acid

NMR (300 MHz, DMSO-$d_6$): δ=1.17 (d, 3H), 2.65 (m, 1H), 2.86 (m, 1H), 3.06 (m, 1H), 7.56 (m, 3H), 8.01 (m, 2H), 12.33 (s, 1H), 13.18 (s, 1H).

Example 17

(R)-3-(5-cyano-4-phenyl-1,3-thiazol-2-ylcarbamoyl)butanoic Acid

NMR (300 MHz, DMSO-$d_6$): δ=1.18 (d, 3H), 2.46 (d, 1H), 2.69 (d, 1H), 3.06 (m, 1H), 7.58 (m, 3H), 8.00 (m, 2H), 12.30 (s, 1H), 13.20 (s, 1H).

Example 18

(S)-3-(5-cyano-4-phenyl-1,3-thiazol-2-ylcarbamoyl)butanoic Acid

NMR (300 MHz, DMSO-$d_6$): δ=1.18 (d, 3H), 2.66 (d, 1H), 2.85 (d, 1H), 3.08 (m, 1H), 7.57 (m, 3H), 8.00 (m, 2H), 12.32 (s, 1H), 13.18 (s, 1H).

Example 19

3-(5-cyano-4-phenyl-1,3-thiazol-2-ylcarbamoyl)cyclohexanecarboxylic Acid

NMR (300 MHz, DMSO-$d_6$): δ=1.31 (m, 3H), 1.50 (m, 1H), 1.90 (m, 3H), 2.08 (m, 1H), 2.28 (m, 1H), 2.62 (m, 1H), 7.56 (m, 3H), 8.01 (m, 2H), 12.20 (s, 1H), 13.09 (s, 1H).

Example 20

4-(5-cyano-4-phenyl-1,3-thiazol-2-ylcarbamoyl)cyclohexanecarboxylic Acid

NMR (300 MHz, DMSO-$d_6$): δ=1.37 (m, 2H), 1.46 (m, 2H), 1.97 (t, 4H), 2.23 (t, 1H), 2.56 (m, 1H), 7.57 (m, 3H), 8.01 (m, 2H), 12.16 (s, 1H), 13.08 (s, 1H).

Example 21

4-(5-cyano-4-phenyl-1,3-thiazol-2-ylcarbamoyl)bicyclo[2.2.2]octane-1-carboxylic Acid NMR (300 MHz, DMSO-$d_6$): δ=1.49 (m, 6H), 1.83 (m, 6H), 7.57 (m, 3H), 7.99 (m, 2H), 12.06 (s, 1H), 13.09 (s, 1H).

Example 22

4-(5-cyano-4-phenyl-1,3-thiazol-2-ylcarbamoyl)-1,4-dimethyl cyclohexanecarboxylic Acid NMR (300 MHz, DMSO-$d_6$): δ=1.23 (s, 3H), 1.31 (s, 3H), 1.43 (m, 4H), 1.94 (m, 4H), 7.57 (m, 3H), 7.99 (m, 2H), 12.06 (s, 1H), 13.08 (s, 1H).

Example 23

4-(5-cyano-4-phenyl-1,3-thiazol-2-ylcarbamoyl)-3-methylbutanoic Acid

NMR (300 MHz, DMSO-$d_6$): δ=0.96 (d, 3H), 2.17 (m, 1H), 2.24 (m, 1H), 2.32 (m, 1H), 2.37 (m, 1H), 2.43 (m, 1H), 7.56 (m, 3H), 8.01 (m, 2H), 12.17 (s, 1H), 13.11 (s, 1H).

Derivatives of Intermediate 2

$R^1$=3-Methylphenyl

Example 24

Cis-3-[5-cyano-4-(3-methylphenyl)-1,3-thiazol-2-ylcarbamoyl]cyclohexanecarboxylic Acid The compound has been synthesized using the anhydride as acylating agent.

NMR (300 MHz, DMSO-$d_6$): δ=1.32 (m, 3H), 1.51 (m, 1H), 1.90 (m, 3H), 2.09 (m, 1H), 2.29 (m, 1H), 2.39 (s, 3H), 2.63 (m, 1H), 7.38 (m, 1H), 7.48 (t, 1H), 7.85 (m, 2H), 12.2 (s, 1H), 13.1 (s, 1H).

Derivatives of the Intermediate 3

$R^1$=2-Chlorophenyl

Example 25

4-[4-(2-chlorophenyl)-5-cyano-1,3-thiazol-2-ylcarbamoyl]-4-methylpentanoic Acid

NMR (300 MHz, DMSO-$d_6$): δ=1.26 (s, 6H), 1.93 (t, 2H), 2.15 (t, 2H), 7.60 (m, 4H), 12.16 (s, 1H), 12.91 (s, 1H).

Example 26

Cis-3-[4-(2-chlorophenyl)-5-cyano-1,3-thiazol-2-ylcarbamoyl]cyclohexanecarboxylic Acid The compound has been synthesized using the anhydride as acylating agent.
NMR (300 MHz, DMSO-$d_6$): δ=1.33 (m, 3H), 1.48 (m, 1H), 1.89 (m, 3H), 2.07 (m, 1H), 2.27 (m, 1H), 2.61 (m, 1H), 7.57 (m, 4H), 12.17 (s, 1H), 13.08 (s, 1H).

Example 27

4-[4-(2-chlorophenyl)-5-cyano-1,3-thiazol-2-ylcarbamoyl]cyclohexane Carboxylic Acid NMR (300 MHz, DMSO-$d_6$): δ=1.46 (m, 4H), 1.95 (m, 4H), 2.21 (m, 1H), 2.65 (m, 1H), 7.60 (m, 4H), 12.15 (s, 1H), 13.07 (s, 1H).

Example 28

3-[4-(2-chlorophenyl)-5-cyano-1,3-thiazol-2-ylcarbamoyl]-3-methylbutanoic Acid

NMR (300 MHz, DMSO-$d_6$): δ=1.24 (s, 6H), 2.78 (s, 2H), 7.60 (m, 4H), 12.29 (s, 1H), 13.10 (s, 1H).

Derivatives of the Intermediate 4

$R^1$=3-Chlorophenyl

Example 29

4-[4-(3-chlorophenyl)-5-cyano-1,3-thiazol-2-ylcarbamoyl]-4-methylpentanoic Acid

NMR (300 MHz, DMSO-$d_6$): δ=1.26 (s, 6H), 1.96 (m, 2H), 2.15 (m, 2H), 7.63 (d, 2H), 7.96 (m, 1H), 7.99 (s, 1H), 12.18 (s, 1H), 12.90 (s, 1H).

Example 28

4-[4-(3-chlorophenyl)-5-cyano-1,3-thiazol-2-ylcarbamoyl]butanoic Acid

NMR (300 MHz, DMSO-$d_6$): δ=1.85 (q, 2H), 2.31 (t, 2H), 2.59 (t, 2H), 7.63 (d, 2H), 7.96 (m, 1H), 7.99 (s, 1H), 12.17 (s, 1H), 13.10 (s, 1H).

Example 29

Cis-3-[4-(3-chlorophenyl)-5-cyano-1,3-thiazol-2-ylcarbamoyl]cyclopentanecarboxylic Acid NMR (300 MHz, DMSO-$d_6$): δ=1.89 (m, 4H), 1.99 (m, 1H), 2.22 (m, 1H), 2.80 (m, 1H), 3.06 (m, 1H), 7.62 (d, 2H), 7.96 (m, 1H), 7.99 (s, 1H), 12.38 (s, 1H), 12.90 (s, 1H).

Example 30 trans-3-[4-(3-chlorophenyl)-5-cyano-1,3-thiazol-2-ylcarbamoyl]cyclopentanecarboxylic Acid NMR (300 MHz, DMSO-$d_6$): δ=1.79 (m, 2H), 2.08 (m, 4H), 2.87 (m, 1H), 3.14 (m, 1H), 7.63 (d, 2H), 7.96 (m, 1H), 7.99 (s, 1H), 12.20 (s, 1H), 13.09 (s, 1H).

Example 31

Cis-2-[4-(3-chlorophenyl)-5-cyano-1,3-thiazol-2-ylcarbamoyl]cyclohexanecarboxylic Acid The compound has been synthesized using the anhydride as acylating agent.
NMR (300 MHz, DMSO-$d_6$): δ=1.39 (m, 3H), 1.65 (m, 1H), 1.78 (m, 2H), 1.93 (m, 1H), 2.09 (m, 1H), 2.80 (m, 1H), 3.12 (m, 1H), 7.63 (d, 2H), 7.97 (m, 1H), 8.00 (s, 1H), 12.46 (s, 1H), 12.98 (s, 1H).

Example 32 trans-2-[4-(3-chlorophenyl)-5-cyano-1,3-thiazol-2-ylcarbamoyl]cyclohexanecarboxylic Acid NMR (300 MHz, DMSO-$d_6$): δ=1.39 (m, 3H), 1.65 (m, 1H), 1.77 (m, 2H), 1.94 (m, 1H), 2.10 (m, 1H), 2.80 (m, 1H), 3.13 (m, 1H), 7.63 (d, 2H), 7.97 (m, 1H), 8.00 (s, 1H), 12.29 (s, 1H), 13.06 (s, 1H).

Example 33

Cis-3-[4-(3-chlorophenyl)-5-cyano-1,3-thiazol-2-ylcarbamoyl]cyclohexanecarboxylic Acid The compound has been synthesized using the anhydride as acylating agent.
NMR (300 MHz, DMSO-$d_6$): δ=1.31 (m, 3H), 1.49 (q, 1H), 1.89 (m, 3H), 2.08 (m, 1H), 2.28 (m, 1H), 2.61 (m, 1H), 7.62 (d, 2H), 7.96 (m, 1H), 7.99 (s, 1H), 12.18 (s, 1H), 13.10 (s, 1H).

Example 34 trans-3-[4-(3-chlorophenyl)-5-cyano-1,3-thiazol-2-ylcarbamoyl]cyclohexanecarboxylic Acid NMR (300 MHz, DMSO-$d_6$): δ=1.31 (m, 3H), 1.49 (q, 1H), 1.89 (m, 3H), 2.09 (m, 1H), 2.28 (m, 1H), 2.61 (m, 1H), 7.62 (d, 2H), 7.96 (m, 1H), 7.99 (s, 1H), 12.25 (s, 1H), 13.11 (s, 1H).

Example 35

Cis-4-[4-(3-chlorophenyl)-5-cyano-1,3-thiazol-2-ylcarbamoyl]cyclohexanecarboxylic Acid NMR (300 MHz, DMSO-$d_6$): δ=1.58 (m, 2H), 1.70 (m, 4), 1.97 (m, 2H), 2.56 (m, 1H), 2.68 (m, 1H), 7.62 (d, 2H), 7.96 (m, 1H), 7.99 (s, 1H), 12.19 (s, 1H), 13.01 (s, 1H).

Example 36 trans-4-[4-(3-chlorophenyl)-5-cyano-1,3-thiazol-2-ylcarbamoyl]cyclohexanecarboxylic Acid NMR (300 MHz, DMSO-$d_6$): δ=1.37 (m, 2H), 1.45 (m, 2H), 1.97 (t, 4H), 2.23 (t, 1H), 2.56 (m, 1H), 7.63 (d, 2H), 7.97 (m, 1H), 8.00 (s, 1H), 12.20 (s, 1H), 13.03 (s, 1H).

Example 37

4-[4-(3-chlorophenyl)-5-cyano-1,3-thiazol-2-ylcarbamoyl]pentanoic Acid

NMR (300 MHz, DMSO-$d_6$): δ=1.16 (d, 3H), 1.71 (m, 1H), 1.88 (m, 1H), 2.23 (m, 2H), 2.73 (m, 1H), 7.63 (d, 2H), 7.97 (m, 1H), 8.00 (s, 1H), 12.19 (s, 1H), 13.16 (s, 1H).

Example 38

(R)-4-[4-(3-chlorophenyl)-5-cyano-1,3-thiazol-2-ylcarbamoyl]pentanoic Acid

NMR (300 MHz, DMSO-$d_6$): δ=1.16 (d, 3H), 1.72 (m, 1H), 1.88 (m, 1H), 2.23 (m, 2H), 2.71 (m, 1H), 7.63 (d, 2H), 7.97 (m, 1H), 8.00 (s, 1H), 12.19 (s, 1H), 13.17 (s, 1H).

Example 39

(S)-4-[4-(3-chlorophenyl)-5-cyano-1,3-thiazol-2-ylcarbamoyl]pentanoic Acid

NMR (300 MHz, DMSO-$d_6$): δ=1.16 (d, 3H), 1.72 (m, 1H), 1.88 (m, 1H), 2.23 (m, 2H), 2.73 (m, 1H), 7.62 (d, 2H), 7.96 (m, 1H), 7.99 (s, 1H), 12.17 (s, 1H), 13.16 (s, 1H).

Example 40

3-[4-(3-chlorophenyl)-5-cyano-1,3-thiazol-2-ylcarbamoyl]-3-methylbutanoic Acid

NMR (300 MHz, DMSO-$d_6$): δ=1.23 (s, 6H), 2.77 (s, 2H), 7.62 (d, 2H), 7.96 (m, 1H), 7.99 (s, 1H), 12.35 (s, 1H), 13.09 (s, 1H).

Example 41

3-[4-(3-chlorophenyl)-5-cyano-1,3-thiazol-2-ylcarbamoyl]butanoic Acid

NMR (300 MHz, DMSO-$d_6$): δ=1.17 (d, 3H), 2.66 (m, 1H), 2.86 (m, 1H), 3.07 (m, 1H), 7.63 (d, 2H), 7.96 (m, 1H), 7.99 (s, 1H), 12.34 (s, 1H), 13.19 (s, 1H).

Example 42

(R)-3-[4-(3-chlorophenyl)-5-cyano-1,3-thiazol-2-ylcarbamoyl]butanoic Acid

NMR (300 MHz, DMSO-$d_6$): δ=1.18 (d, 3H), 2.46 (d, 1H), 2.71 (d, 1H), 3.08 (m, 1H), 7.62 (d, 2H), 7.96 (m, 1H), 7.99 (s, 1H), 12.35 (s, 1H), 13.22 (s, 1H).

Example 43

(S)-3-[4-(3-chlorophenyl)-5-cyano-1,3-thiazol-2-ylcarbamoyl]butanoic Acid

NMR (300 MHz, DMSO-$d_6$): δ=1.17 (d, 3H), 2.65 (m, 1H), 2.85 (m, 1H), 3.07 (m, 1H), 7.62 (d, 2H), 7.96 (m, 1H), 7.99 (s, 1H), 12.33 (s, 1H), 13.19 (s, 1H).

Example 44

3-[4-(3-chlorophenyl)-5-cyano-1,3-thiazol-2-ylcarbamoyl]cyclohexane Carboxylic Acid NMR (300 MHz, DMSO-$d_6$): δ=1.31 (m, 3H), 1.49 (m, 1H), 1.89 (m, 3H), 2.09 (m, 1H), 2.28 (m, 1H), 2.61 (m, 1H), 7.63 (m, 2H), 8.01 (m, 2H), 12.24 (s, 1H), 13.11 (s, 1H).

Example 45

4-[4-(3-chlorophenyl)-5-cyano-1,3-thiazol-2-ylcarbamoyl]cyclohexane Carboxylic Acid NMR (300 MHz, DMSO-$d_6$): δ=1.41 (m, 4H), 1.97 (m, 4H), 2.23 (m, 1H), 2.67 (m, 1H), 7.63 (m, 2H), 7.99 (m, 2H), 12.22 (s, 1H), 12.99 (s, 1H).

Example 46

4-[4-(3-chlorophenyl)-5-cyano-1,3-thiazol-2-ylcarbamoyl]bicyclo[2.2.2]octane-1-carboxylic Acid NMR (300 MHz, DMSO-$d_6$): δ=1.47 (m, 6H), 1.81 (m, 6H), 7.63 (m, 2H), 7.97 (m, 2H), 12.16 (s, 1H), 13.10 (s, 1H).

Derivatives of the Intermediate 5

$R^1$=2-Fluorophenyl

Example 47

4-[5-cyano-4-(2-fluorophenyl)-1,3-thiazol-2-ylcarbamoyl]-4-methylpentanoic Acid

NMR (300 MHz, DMSO-$d_6$): δ=1.26 (s, 6H), 1.95 (m, 2H), 2.15 (m, 2H), 7.39 (dd, 1H), 7.45 (d, 1H), 7.61 (m, 1H), 7.72 (m, 1H), 12.16 (s, 1H), 12.90 (s, 1H).

Example 48

4-[5-cyano-4-(2-fluorophenyl)-1,3-thiazol-2-ylcarbamoyl]butanoic Acid

NMR (300 MHz, DMSO-$d_6$): δ=1.85 (q, 2H), 2.31 (t, 2H), 2.59 (t, 2H), 7.39 (dd, 1H), 7.45 (d, 1H), 7.61 (m, 1H), 7.72 (m, 1H), 12.14 (s, 1H), 13.11 (s, 1H).

Example 49

4-[5-cyano-4-(2-fluorophenyl)-1,3-thiazol-2-ylcarbamoyl]-3-methylbutanoic Acid

NMR (300 MHz, DMSO-$d_6$): δ=0.96 (d, 3H), 2.16 (m, 1H), 2.23 (m, 1H), 2.31 (m, 1H), 2.36 (m, 1H), 2.42 (m, 1H), 7.39 (dd, 1H), 7.45 (d, 1H), 7.61 (m, 1H), 7.72 (m, 1H), 12.15 (s, 1H), 13.09 (s, 1H).

Example 50

Cis-3-[5-cyano-4-(2-fluorophenyl)-1,3-thiazol-2-ylcarbamoyl]cyclopentanecarboxylic Acid NMR (300 MHz, DMSO-$d_6$): δ=1.89 (m, 4H), 2.01 (m, 1H), 2.23 (m, 1H), 2.80 (m, 1H), 3.08 (m, 1H), 7.39 (dd, 1H), 7.45 (d, 1H), 7.61 (m, 1H), 7.72 (m, 1H), 12.35 (s, 1H), 12.90 (s, 1H).

Example 51 trans-3-[5-cyano-4-(2-fluorophenyl)-1,3-thiazol-2-ylcarbamoyl]cyclopentanecarboxylic Acid NMR (300 MHz, DMSO-$d_6$): δ=1.79 (m, 2H), 2.09 (m, 4H), 2.88 (m, 1H), 3.15 (m, 1H), 7.39 (dd, 1H), 7.45 (d, 1H), 7.61 (m, 1H), 7.72 (m, 1H), 12.17 (s, 1H), 13.09 (s, 1H).

Example 52

Cis-2-[5-cyano-4-(2-fluorophenyl)-1,3-thiazol-2-ylcarbamoyl]cyclohexanecarboxylic Acid NMR (300 MHz, DMSO-$d_6$): δ=1.36 (m, 3H), 1.62 (m, 1H), 1.76 (m, 2H), 1.92 (m, 1H), 2.08 (m, 1H), 2.79 (m, 1H), 3.12 (m, 1H), 7.39 (dd, 1H), 7.45 (d, 1H), 7.61 (m, 1H), 7.72 (m, 1H), 12.35 (s, 1H), 12.96 (s, 1H).

Example 53 trans-2-[5-cyano-4-(2-fluorophenyl)-1,3-thiazol-2-ylcarbamoyl]cyclohexanecarboxylic Acid NMR (300 MHz, DMSO-$d_6$): δ=1.37 (m, 3H), 1.63 (m, 1H), 1.77 (m, 2H), 1.92 (m, 1H), 2.09 (m, 1H), 2.80 (m, 1H), 3.12 (m, 1H), 7.39 (dd, 1H), 7.45 (d, 1H), 7.61 (m, 1H), 7.72 (m, 1H), 12.22 (s, 1H), 13.04 (s, 1H).

Example 54

Cis-3-[5-cyano-4-(2-fluorophenyl)-1,3-thiazol-2-ylcarbamoyl]cyclohexanecarboxylic Acid The compound has been synthesized using the anhydride as acylating agent.

NMR (300 MHz, DMSO-$d_6$): δ=1.33 (m, 3H), 1.47 (q, 1H), 1.90 (m, 3H), 2.08 (d, 1H), 2.27 (m, 1H), 2.61 (m, 1H), 7.40 (q, 1H), 7.45 (d, 1H), 7.61 (m, 1H), 7.71 (m, 1H), 12.22 (s, 1H), 13.11 (s, 1H).

Example 55 trans-3-[5-cyano-4-(2-fluorophenyl)-1,3-thiazol-2-ylcarbamoyl]cyclohexanecarboxylic Acid NMR (300 MHz, DMSO-$d_6$): δ=1.32 (m, 3H), 1.48 (q, 1H), 1.90 (m, 3H), 2.09 (d, 1H), 2.27 (m, 1H), 2.61 (m, 1H), 7.40 (q, 1H), 7.45 (d, 1H), 7.61 (m, 1H), 7.71 (m, 1H), 12.26 (s, 1H), 13.12 (s, 1H).

Example 56

Cis-4-[5-cyano-4-(2-fluorophenyl)-1,3-thiazol-2-ylcarbamoyl]cyclohexanecarboxylic Acid NMR (300 MHz, DMSO-$d_6$): δ=1.55 (m, 2H), 1.70 (m, 4H), 1.96 (m, 2H), 2.23 (t, 1H), 2.67 (m, 1H), 7.39 (dd, 1H), 7.45 (d, 1H), 7.61 (m, 1H), 7.72 (m, 1H), 12.16 (s, 1H), 13.10 (s, 1H).

Example 57 trans-4-[5-cyano-4-(2-fluorophenyl)-1,3-thiazol-2-ylcarbamoyl]cyclohexanecarboxylic Acid NMR (300 MHz, DMSO-$d_6$): δ=1.35 (m, 2H), 1.46 (m, 2H), 1.96 (t, 4H), 2.23 (t, 1H), 2.65 (m, 1H), 7.39 (dd, 1H), 7.45 (d, 1H), 7.61 (m, 1H), 7.72 (m, 1H), 12.15 (s, 1H), 13.09 (s, 1H).

Example 58

4-[5-cyano-4-(2-fluorophenyl)-1,3-thiazol-2-ylcarbamoyl]pentanoic Acid

NMR (300 MHz, DMSO-$d_6$): δ=1.17 (d, 3H), 1.68 (m, 1H), 1.86 (m, 1H), 2.23 (m, 2H), 2.72 (m, 1H), 7.39 (dd, 1H), 7.45 (d, 1H), 7.61 (m, 1H), 7.72 (m, 1H), 12.19 (s, 1H), 13.20 (s, 1H).

Example 59

(R)-4-[5-cyano-4-(2-fluorophenyl)-1,3-thiazol-2-ylcarbamoyl]pentanoic Acid

NMR (300 MHz, DMSO-$d_6$): δ=1.16 (d, 3H), 1.69 (m, 1H), 1.87 (m, 1H), 2.23 (m, 2H), 2.71 (m, 1H), 7.39 (dd, 1H), 7.45 (d, 1H), 7.61 (m, 1H), 7.72 (m, 1H), 12.17 (s, 1H), 13.14 (s, 1H).

Example 60

(S)-4-[5-cyano-4-(2-fluorophenyl)-1,3-thiazol-2-ylcarbamoyl]pentanoic Acid

NMR (300 MHz, DMSO-$d_6$): δ=1.15 (d, 3H), 1.67 (m, 1H), 1.86 (m, 1H), 2.23 (m, 2H), 2.72 (m, 1H), 7.39 (dd, 1H), 7.45 (d, 1H), 7.61 (m, 1H), 7.72 (m, 1H), 12.17 (s, 1H), 13.18 (s, 1H).

Example 61

3-[5-cyano-4-(2-fluorophenyl)-1,3-thiazol-2-ylcarbamoyl]-3-methylbutanoic Acid

NMR (300 MHz, DMSO-$d_6$): δ=1.23 (s, 6H), 2.77 (s, 2H), 7.39 (dd, 1H), 7.45 (d, 1H), 7.61 (m, 1H), 7.72 (m, 1H), 12.28 (s, 1H), 13.11 (s, 1H).

Example 62

3-[5-cyano-4-(2-fluorophenyl)-1,3-thiazol-2-ylcarbamoyl]butanoic Acid

NMR (300 MHz, DMSO-$d_6$): δ=1.17 (d, 3H), 2.65 (m, 1H), 2.86 (m, 1H), 3.05 (m, 1H), 7.39 (dd, 1H), 7.45 (d, 1H), 7.61 (m, 1H), 7.72 (m, 1H), 12.31 (s, 1H), 13.19 (s, 1H).

Example 63

(R)-3-[5-cyano-4-(2-fluorophenyl)-1,3-thiazol-2-ylcarbamoyl]butanoic Acid

NMR (300 MHz, DMSO-$d_6$): δ=1.18 (d, 3H), 2.45 (m, 1H), 2.69 (m, 1H), 3.05 (m, 1H), 7.39 (dd, 1H), 7.45 (d, 1H), 7.61 (m, 1H), 7.72 (m, 1H), 12.27 (s, 1H), 13.21 (s, 1H).

Example 64

(S)-3-[5-cyano-4-(2-fluorophenyl)-1,3-thiazol-2-ylcarbamoyl]butanoic Acid

NMR (300 MHz, DMSO-$d_6$): δ=1.17 (d, 3H), 2.65 (m, 1H), 2.86 (m, 1H), 3.06 (m, 1H), 7.39 (dd, 1H), 7.45 (d, 1H), 7.61 (m, 1H), 7.72 (m, 1H), 12.28 (s, 1H), 13.17 (s, 1H).

Example 65

3-[5-cyano-4-(2-fluorophenyl)-1,3-thiazol-2-ylcarbamoyl]cyclohexane Carboxylic Acid NMR (300 MHz, DMSO-$d_6$): δ=1.32 (m, 3H), 1.48 (q, 1H), 1.90 (m, 3H), 2.09 (d, 1H), 2.27 (m, 1H), 2.61 (m, 1H), 7.40 (q, 1H), 7.45 (d, 1H), 7.61 (m, 1H), 7.71 (m, 1H), 12.26 (s, 1H), 13.12 (s, 1H).

Example 66

4-[5-cyano-4-(2-fluorophenyl)-1,3-thiazol-2-ylcarbamoyl]cyclohexane Carboxylic Acid NMR (300 MHz, DMSO-$d_6$): δ=1.48 (m, 4H), 1.96 (t, 4H), 2.23 (t, 1H), 2.57 (m, 1H), 7.39 (dd, 1H), 7.45 (d, 1H), 7.61 (m, 1H), 7.72 (m, 1H), 12.15 (s, 1H), 13.09 (s, 1H).

Example 67

4-[5-cyano-4-(2-fluorophenyl)-1,3-thiazol-2-ylcarbamoyl]bicyclo[2.2.2]octane-1-carboxylic Acid NMR (300 MHz, DMSO-$d_6$): δ=1.46 (m, 6H), 1.84 (m, 6H), 7.39 (dd, 1H), 7.45 (d, 1H), 7.61 (m, 1H), 7.72 (m, 1H), 12.05 (s, 1H), 13.08 (s, 1H).

Derivatives of the Intermediate 6

$R^1$=3-Fluorophenyl

Example 68

4-[5-cyano-4-(3-fluorophenyl)-1,3-thiazol-2-ylcarbamoyl]-4-methylpentanoic Acid

NMR (300 MHz, DMSO-$d_6$): δ=1.26 (s, 6H), 1.97 (m, 2H), 2.15 (m, 2H), 7.42 (m, 1H), 7.66 (q, 1H), 7.77 (d, 1H), 7.87 (d, 1H), 12.19 (s, 1H), 12.89 (s, 1H).

Example 69

4-[5-cyano-4-(3-fluorophenyl)-1,3-thiazol-2-ylcarbamoyl]butanoic Acid

NMR (300 MHz, DMSO-$d_6$): δ=1.85 (q, 2H), 2.31 (t, 2H), 2.60 (t, 2H), 7.41 (m, 1H), 7.65 (q, 1H), 7.77 (m, 1H), 7.88 (m, 1H), 12.17 (s, 1H), 13.11 (s, 1H).

Example 70

4-[5-cyano-4-(3-fluorophenyl)-1,3-thiazol-2-ylcarbamoyl]-3-methylbutanoic Acid

NMR (300 MHz, DMSO-$d_6$): δ=0.96 (d, 3H), 2.16 (m, 1H), 2.23 (m, 1H), 2.31 (m, 1H), 2.37 (m, 1H), 2.42 (m, 1H), 7.40 (m, 1H), 7.64 (q, 1H), 7.76 (m, 1H), 7.87 (m, 1H), 12.18 (s, 1H), 13.12 (s, 1H).

Example 71

Cis-3-[5-cyano-4-(3-fluorophenyl)-1,3-thiazol-2-ylcarbamoyl]cyclopentanecarboxylic Acid NMR (300 MHz, DMSO-$d_6$): δ=1.89 (m, 4H), 1.99 (m, 1H), 2.23 (m, 1H), 2.79 (m, 1H), 3.08 (m, 1H), 7.40 (m, 1H), 7.64 (q, 1H), 7.76 (m, 1H), 7.87 (m, 1H), 12.39 (s, 1H), 12.91 (s, 1H).

Example 72 trans-3-[5-cyano-4-(3-fluorophenyl)-1,3-thiazol-2-ylcarbamoyl]cyclopentanecarboxylic Acid NMR (300 MHz, DMSO-$d_6$): δ=1.79 (m, 2H), 2.08 (m, 4H), 2.88 (m, 1H), 3.14 (m, 1H), 7.40 (m, 1H), 7.64 (q, 1H), 7.76 (m, 1H), 7.87 (m, 1H), 12.20 (s, 1H), 13.09 (s, 1H).

Example 73

Cis-2-[5-cyano-4-(3-fluorophenyl)-1,3-thiazol-2-ylcarbamoyl]cyclohexanecarboxylic Acid The compound has been synthesized using the anhydride as acylating agent.

NMR (300 MHz, DMSO-$d_6$): δ=1.39 (m, 3H), 1.65 (m, 1H), 1.77 (m, 2H), 1.938 (m, 1H), 2.09 (m, 1H), 2.81 (m, 1H), 3.12 (m, 1H), 7.39 (m, 1H), 7.63 (q, 1H), 7.76 (m, 1H), 7.87 (m, 1H), 12.42 (s, 1H), 12.95 (s, 1H).

Example 74 trans-2-[5-cyano-4-(3-fluorophenyl)-1,3-thiazol-2-ylcarbamoyl]cyclohexanecarboxylic Acid NMR (300 MHz, DMSO-$d_6$): δ=1.39 (m, 3H), 1.66 (m, 1H), 1.77 (m, 2H), 1.92 (m, 1H), 2.10 (m, 1H), 2.81 (m, 1H), 3.13 (m, 1H), 7.39 (m, 1H), 7.63 (q, 1H), 7.76 (m, 1H), 7.87 (m, 1H), 12.27 (s, 1H), 13.05 (s, 1H).

Example 75

Cis-3-[5-cyano-4-(3-fluorophenyl)-1,3-thiazol-2-ylcarbamoyl]cyclohexanecarboxylic Acid The compound has been synthesized using the anhydride as acylating agent.

NMR (300 MHz, DMSO-d$_6$): δ=1.33 (m, 3H), 1.47 (q, 1H), 1.91 (m, 3H), 2.09 (d, 1H), 2.28 (m, 1H), 2.63 (m, 1H), 7.40 (m, 1H), 7.65 (q, 1H), 7.73 (dd, 1H), 7.85 (m, 1H), 12.17 (s, 1H), 13.11 (s, 1H).

Example 76 trans-3-[5-cyano-4-(3-fluorophenyl)-1,3-thiazol-2-ylcarbamoyl]cyclohexanecarboxylic Acid NMR (300 MHz, DMSO-d$_6$): δ=1.32 (m, 3H), 1.47 (q, 1H), 1.91 (m, 3H), 2.10 (d, 1H), 2.28 (m, 1H), 2.63 (m, 1H), 7.41 (m, 1H), 7.65 (q, 1H), 7.73 (dd, 1H), 7.85 (m, 1H), 12.26 (s, 1H), 13.12 (s, 1H).

Example 77

Cis-4-[5-cyano-4-(3-fluorophenyl)-1,3-thiazol-2-ylcarbamoyl]cyclohexanecarboxylic Acid NMR (300 MHz, DMSO-d$_6$): δ=1.52 (m, 2H), 1.70 (m, 4), 1.95 (m, 2), 2.22 (m, 1H), 2.65 (m, 1H), 7.40 (m, 1H), 7.64 (q, 1H), 7.76 (m, 1H), 7.87 (m, 1H), 12.19 (s, 1H), 13.09 (s, 1H).

Example 78 trans-4-[5-cyano-4-(3-fluorophenyl)-1,3-thiazol-2-ylcarbamoyl]cyclohexanecarboxylic Acid NMR (300 MHz, DMSO-d$_6$): δ=1.34 (m, 2H), 1.46 (m, 2H), 1.97 (t, 4H), 2.23 (t, 1H), 2.55 (m, 1H), 7.42 (m, 1H), 7.65 (q, 1H), 7.74 (dd, 1H), 7.85 (dd, 1H), 12.15 (s, 1H), 13.11 (s, 1H).

Example 79

4-[5-cyano-4-(3-fluorophenyl)-1,3-thiazol-2-ylcarbamoyl]pentanoic Acid

NMR (300 MHz, DMSO-d$_6$): δ=1.16 (d, 3H), 1.71 (m, 1H), 1.87 (m, 1H), 2.24 (m, 2H), 2.73 (m, 1H), 7.41 (m, 1H), 7.65 (q, 1H), 7.74 (m, 1H), 7.85 (m, 1H), 12.19 (s, 1H), 13.15 (s, 1H).

Example 80

(R)-4-[5-cyano-4-(3-fluorophenyl)-1,3-thiazol-2-ylcarbamoyl]pentanoic Acid

NMR (300 MHz, DMSO-d$_6$): δ=1.16 (d, 3H), 1.72 (m, 1H), 1.88 (m, 1H), 2.23 (m, 2H), 2.72 (m, 1H), 7.39 (m, 1H), 7.65 (q, 1H), 7.73 (m, 1H), 7.85 (m, 1H), 12.20 (s, 1H), 13.14 (s, 1H).

Example 81

(S)-4-[5-cyano-4-(3-fluorophenyl)-1,3-thiazol-2-ylcarbamoyl]pentanoic Acid

NMR (300 MHz, DMSO-d$_6$): δ=1.16 (d, 3H), 1.72 (m, 1H), 1.88 (m, 1H), 2.23 (t, 2H), 2.73 (m, 1H), 7.41 (m, 1H), 7.64 (q, 1H), 7.74 (m, 1H), 7.86 (m, 1H), 12.18 (s, 1H), 13.16 (s, 1H).

Example 82

3-[5-cyano-4-(3-fluorophenyl)-1,3-thiazol-2-ylcarbamoyl]-3-methylbutanoic Acid

NMR (300 MHz, DMSO-d$_6$): δ=1.23 (s, 6H), 2.76 (s, 2H), 7.41 (m, 1H), 7.65 (q, 1H), 7.73 (m, 1H), 7.85 (m, 1H), 12.34 (s, 1H), 13.12 (s, 1H).

Example 83

3-[5-cyano-4-(3-fluorophenyl)-1,3-thiazol-2-ylcarbamoyl]butanoic Acid

NMR (300 MHz, DMSO-d$_6$): δ=1.17 (d, 3H), 2.66 (m, 1H), 2.87 (m, 1H), 3.09 (m, 1H), 7.42 (m, 1H), 7.65 (q, 1H), 7.74 (dd, 1H), 7.86 (d, 1H), 12.34 (s, 1H), 13.21 (s, 1H).

Example 84

(R)-3-[5-cyano-4-(3-fluorophenyl)-1,3-thiazol-2-ylcarbamoyl]butanoic Acid

NMR (300 MHz, DMSO-d$_6$): δ=1.18 (d, 3H), 2.45 (m, 1H), 2.69 (m, 1H), 3.07 (m, 1H), 7.40 (m, 1H), 7.64 (q, 1H), 7.76 (m, 1H), 7.87 (m, 1H), 12.31 (s, 1H), 13.22 (s, 1H).

Example 85

(S)-3-[5-cyano-4-(3-fluorophenyl)-1,3-thiazol-2-ylcarbamoyl]butanoic Acid

NMR (300 MHz, DMSO-d$_6$): δ=1.17 (d, 3H), 2.65 (m, 1H), 2.86 (m, 1H), 3.10 (m, 1H), 7.41 (m, 1H), 7.64 (q, 1H), 7.75 (m, 1H), 7.86 (m, 1H), 12.33 (s, 1H), 13.20 (s, 1H).

Example 86

3-[5-cyano-4-(3-fluorophenyl)-1,3-thiazol-2-ylcarbamoyl]cyclohexane carboxylic Acid NMR (300 MHz, DMSO-d$_6$): δ=1.32 (m, 3H), 1.48 (m, 1H), 1.90 (m, 3H), 2.10 (m, 1H), 2.29 (m, 1H), 2.63 (m, 1H), 7.42 (m, 1H), 7.65 (q, 1H), 7.74 (dd, 1H), 7.86 (d, 1H), 12.25 (s, 1H), 13.12 (s, 1H).

Example 87

4-[5-cyano-4-(3-fluorophenyl)-1,3-thiazol-2-ylcarbamoyl]cyclohexane Carboxylic Acid NMR (300 MHz, DMSO-d$_6$): δ=1.47 (m, 4H), 1.96 (t, 4H), 2.23 (t, 1H), 2.57 (m, 1H), 7.42 (m, 1H), 7.65 (q, 1H), 7.74 (dd, 1H), 7.86 (d, 1H), 12.16 (s, 1H), 13.11 (s, 1H).

Example 88

4-[5-cyano-4-(3-fluorophenyl)-1,3-thiazol-2-ylcarbamoyl]bicyclo[2.2.2]octane-1-carboxylic Acid NMR (300 MHz, DMSO-d$_6$): δ=1.50 (m, 6H), 1.84 (m, 6H), 7.42 (m, 1H), 7.65 (q, 1H), 7.74 (dd, 1H), 7.86 (d, 1H), 12.08 (s, 1H), 13.11 (s, 1H).

Derivatives of the Intermediate 7

R¹=4-Fluorophenyl

Example 89

4-[5-cyano-4-(4-fluorophenyl)-1,3-thiazol-2-ylcarbamoyl]-4-methylpentanoic Acid

NMR (300 MHz, DMSO-$d_6$): δ=1.26 (s, 6H), 1.96 (m, 2H), 2.15 (m, 2H), 7.39 (t, 2H), 8.03 (m, 2H), 12.18 (s, 1H), 12.88 (s, 1H).

Example 90

4-[5-cyano-4-(4-fluorophenyl)-1,3-thiazol-2-ylcarbamoyl]butanoic Acid

NMR (300 MHz, DMSO-$d_6$): δ=1.85 (q, 2H), 2.31 (t, 2H), 2.59 (t, 2H), 7.39 (t, 2H), 8.02 (m, 2H), 12.17 (s, 1H), 13.10 (s, 1H).

Example 91

4-[5-cyano-4-(4-fluorophenyl)-1,3-thiazol-2-ylcarbamoyl]-3-methylbutanoic Acid

NMR (300 MHz, DMSO-$d_6$): δ=0.96 (d, 3H), 2.17 (m, 1H), 2.24 (m, 1H), 2.32 (m, 1H), 2.37 (m, 1H), 2.43 (m, 1H), 7.39 (t, 2H), 8.03 (m, 2H), 12.19 (s, 1H), 13.12 (s, 1H).

Example 92

Cis-3-[5-cyano-4-(4-fluorophenyl)-1,3-thiazol-2-ylcarbamoyl]cyclopentanecarboxylic Acid NMR (300 MHz, DMSO-$d_6$): δ=1.88 (m, 4H), 1.99 (m, 1H), 2.23 (m, 1H), 2.79 (m, 1H), 3.06 (m, 1H), 7.39 (t, 2H), 8.03 (m, 2H), 12.38 (s, 1H), 12.92 (s, 1H).

Example 93 trans-3-[5-cyano-4-(4-fluorophenyl)-1,3-thiazol-2-ylcarbamoyl]cyclopentanecarboxylic Acid NMR (300 MHz, DMSO-$d_6$): δ=1.78 (m, 2H), 2.08 (m, 4H), 2.89 (m, 1H), 3.15 (m, 1H), 7.39 (t, 2H), 8.03 (m, 2H), 12.21 (s, 1H), 13.10 (s, 1H).

Example 94

Cis-2-[5-cyano-4-(4-fluorophenyl)-1,3-thiazol-2-ylcarbamoyl]cyclohexanecarboxylic Acid The compound has been synthesized using the anhydride as acylating agent.
NMR (300 MHz, DMSO-$d_6$): δ=1.38 (m, 3H), 1.64 (m, 1H), 1.77 (m, 2H), 1.92 (m, 1H), 2.07 (m, 1H), 2.80 (m, 1H), 3.12 (m, 1H), 7.39 (t, 2H), 8.03 (m, 2H), 12.42 (s, 1H), 12.97 (s, 1H).

Example 95 trans-2-[5-cyano-4-(4-fluorophenyl)-1,3-thiazol-2-ylcarbamoyl]cyclohexanecarboxylic Acid NMR (300 MHz, DMSO-$d_6$): δ=1.38 (m, 3H), 1.65 (m, 1H), 1.76 (m, 2H), 1.92 (m, 1H), 2.10 (m, 1H), 2.80 (m, 1H), 3.13 (m, 1H), 7.39 (t, 2H), 8.03 (m, 2H), 12.27 (s, 1H), 13.05 (s, 1H).

Example 96

Cis-3-[5-cyano-4-(4-fluorophenyl)-1,3-thiazol-2-ylcarbamoyl]cyclohexanecarboxylic Acid The compound has been synthesized using the anhydride as acylating agent.
NMR (300 MHz, DMSO-$d_6$): δ=1.32 (m, 3H), 1.47 (q, 1H), 1.90 (m, 3H), 2.09 (d, 1H), 2.28 (m, 1H), 2.63 (m, 1H), 7.39 (t, 2H), 8.03 (m, 2H), 12.18 (s, 1H), 13.11 (s, 1H).

Example 97 trans-3-[5-cyano-4-(4-fluorophenyl)-1,3-thiazol-2-ylcarbamoyl]cyclohexanecarboxylic Acid NMR (300 MHz, DMSO-$d_6$): δ=1.31 (m, 3H), 1.47 (q, 1H), 1.90 (m, 3H), 2.09 (d, 1H), 2.28 (m, 1H), 2.63 (m, 1H), 7.39 (t, 2H), 8.03 (m, 2H), 12.24 (s, 1H), 13.10 (s, 1H).

Example 98

Cis-4-[5-cyano-4-(4-fluorophenyl)-1,3-thiazol-2-ylcarbamoyl]cyclohexanecarboxylic Acid NMR (300 MHz, DMSO-$d_6$): δ=1.56 (m, 2H), 1.70 (m, 4), 1.95 (m, 2), 2.22 (m, 1H), 2.57 (m, 1H), 7.39 (t, 2H), 8.03 (m, 2H), 12.6 (s, 1H), 13.10 (s, 1H).

Example 99 trans-4-[5-cyano-4-(4-fluorophenyl)-1,3-thiazol-2-ylcarbamoyl]cyclohexanecarboxylic Acid NMR (300 MHz, DMSO-$d_6$): δ=1.37 (m, 2H), 1.46 (m, 2), 1.96 (m, 4), 2.23 (m, 1H), 2.57 (m, 1H), 7.39 (t, 2H), 8.02 (m, 2H), 12.18 (s, 1H), 13.09 (s, 1H).

Example 100

4-[5-cyano-4-(4-fluorophenyl)-1,3-thiazol-2-ylcarbamoyl]pentanoic Acid

NMR (300 MHz, DMSO-$d_6$): δ=1.17 (d, 3H), 1.72 (m, 1H), 1.87 (m, 1H), 2.23 (m, 2H), 2.74 (m, 1H), 7.39 (t, 2H), 8.03 (m, 2H), 12.19 (s, 1H), 13.18 (s, 1H).

Example 101

(R)-4-[5-cyano-4-(4-fluorophenyl)-1,3-thiazol-2-ylcarbamoyl]pentanoic Acid

NMR (300 MHz, DMSO-$d_6$): δ=1.16 (d, 3H), 1.73 (m, 1H), 1.88 (m, 1H), 2.24 (m, 2H), 2.73 (m, 1H), 7.39 (t, 2H), 8.03 (m, 2H), 12.17 (s, 1H), 13.14 (s, 1H).

Example 102

(S)-4-[5-cyano-4-(4-fluorophenyl)-1,3-thiazol-2-ylcarbamoyl]pentanoic Acid

NMR (300 MHz, DMSO-$d_6$): δ=1.17 (d, 3H), 1.72 (m, 1H), 1.88 (m, 1H), 2.23 (m, 2H), 2.74 (m, 1H), 7.39 (t, 2H), 8.03 (m, 2H), 12.18 (s, 1H), 13.16 (s, 1H).

Example 103

3-[5-cyano-4-(4-fluorophenyl)-1,3-thiazol-2-ylcarbamoyl]-3-methylbutanoic Acid

NMR (300 MHz, DMSO-$d_6$): δ=1.23 (s, 6H), 2.78 (s, 2H), 7.39 (t, 2H), 8.03 (m, 2H), 12.35 (s, 1H), 13.10 (s, 1H).

Example 104

3-[5-cyano-4-(4-fluorophenyl)-1,3-thiazol-2-ylcarbamoyl]butanoic Acid

NMR (300 MHz, DMSO-$d_6$): δ=1.17 (d, 3H), 2.65 (m, 1H), 2.86 (m, 1H), 3.08 (m, 1H), 7.39 (t, 2H), 8.03 (m, 2H), 12.34 (s, 1H), 13.20 (s, 1H).

Example 105

(R)-3-[5-cyano-4-(4-fluorophenyl)-1,3-thiazol-2-ylcarbamoyl]butanoic Acid

NMR (300 MHz, DMSO-$d_6$): δ=1.18 (d, 3H), 2.45 (m, 1H), 2.70 (m, 1H), 3.06 (m, 1H), 7.39 (t, 2H), 8.03 (m, 2H), 12.31 (s, 1H), 13.22 (s, 1H).

Example 106

(S)-3-[5-cyano-4-(4-fluorophenyl)-1,3-thiazol-2-ylcarbamoyl]butanoic Acid

NMR (300 MHz, DMSO-$d_6$): δ=1.17 (d, 3H), 2.65 (m, 1H), 2.86 (m, 1H), 3.08 (m, 1H), 7.39 (t, 2H), 8.04 (m, 2H), 12.32 (s, 1H), 13.19 (s, 1H).

Example 107

3-[5-cyano-4-(4-fluorophenyl)-1,3-thiazol-2-ylcarbamoyl]cyclohexane Carboxylic Acid NMR (300 MHz, DMSO-$d_6$): δ=1.32 (m, 3H), 1.51 (m, 1H), 1.90 (m, 3H), 2.09 (m, 1H), 2.28 (m, 1H), 2.63 (m, 1H), 7.37 (t, 2H), 8.02 (m, 2H), 12.24 (s, 1H), 13.10 (s, 1H).

Example 108

4-[5-cyano-4-(4-fluorophenyl)-1,3-thiazol-2-ylcarbamoyl]cyclohexane Carboxylic Acid NMR (300 MHz, DMSO-$d_6$): δ=1.48 (m, 4H), 1.96 (t, 4H), 2.23 (t, 1H), 2.56 (m, 1H), 7.39 (t, 2H), 8.04 (m, 2H), 12.16 (s, 1H), 13.08 (s, 1H).

Example 109

4-[5-cyano-4-(4-fluorophenyl)-1,3-thiazol-2-ylcarbamoyl]bicyclo[2.2.2]octane-1-carboxylic Acid NMR (300 MHz, DMSO-$d_6$): δ=1.50 (m, 6H), 1.83 (m, 6H), 7.40 (t, 2H), 8.06 (m, 2H), 12.07 (s, 1H), 13.10 (s, 1H).

Derivatives of the Intermediate 8

$R^1$=3,4-Difluorophenyl

Example 110

4-[5-cyano-4-(3,4-difluorophenyl)-1,3-thiazol-2-ylcarbamoyl]-4-methylpentanoic Acid NMR (300 MHz, DMSO-$d_6$): δ=1.26 (s, 6H), 1.94 (m, 2H), 2.15 (m, 2H), 7.69 (q, 1H), 7.86 (m, 1H), 7.95 (m, 1H), 12.16 (s, 1H), 12.90 (s, 1H).

Example 111

Cis-3-[5-cyano-4-(3,4-difluorophenyl)-1,3-thiazol-2-ylcarbamoyl]cyclohexanecarboxylic Acid The compound has been synthesized using the anhydride as acylating agent.

NMR (300 MHz, DMSO-$d_6$): δ=1.33 (m, 3H), 1.47 (q, 1H), 1.91 (m, 3H), 2.09 (d, 1H), 2.28 (m, 1H), 2.63 (m, 1H), 7.69 (q, 1H), 7.86 (m, 1H), 7.95 (m, 1H), 12.24 (s, 1H), 13.12 (s, 1H).

Example 112

4-[5-cyano-4-(3,4-difluorophenyl)-1,3-thiazol-2-ylcarbamoyl]cyclohexanecarboxylic Acid NMR (300 MHz, DMSO-$d_6$): δ=1.51 (m, 4H), 1.95 (t, 4H), 2.23 (t, 1H), 2.56 (m, 1H), 7.69 (q, 1H), 7.87 (m, 1H), 7.96 (m, 1H), 12.16 (s, 1H), 13.11 (s, 1H).

Derivatives of the Intermediate 9

$R^1$=3,5-Difluorophenyl

Example 113

4-[5-cyano-4-(3,5-difluorophenyl)-1,3-thiazol-2-ylcarbamoyl]-4-methylpentanoic Acid NMR (300 MHz, DMSO-$d_6$): δ=1.26 (s, 6H), 1.94 (m, 2H), 2.15 (m, 2H), 7.50 (m, 1H), 7.64 (dd, 2H), 12.16 (s, 1H), 12.89 (s, 1H).

Example 114

Cis-3-[5-cyano-4-(3,5-difluorophenyl)-1,3-thiazol-2-ylcarbamoyl]cyclohexanecarboxylic Acid The compound has been synthesized using the anhydride as acylating agent.

NMR (300 MHz, DMSO-$d_6$): δ=1.34 (m, 3H), 1.47 (q, 1H), 1.90 (m, 3H), 2.09 (d, 1H), 2.28 (m, 1H), 2.63 (m, 1H), 7.49 (m, 1H), 7.63 (dd, 2H), 12.17 (s, 1H), 13.13 (s, 1H).

Example 115

4-[5-cyano-4-(3,5-difluorophenyl)-1,3-thiazol-2-ylcarbamoyl]cyclohexanecarboxylic Acid NMR (300 MHz, DMSO-$d_6$): δ=1.50 (m, 4H), 1.96 (t, 4H), 2.23 (t, 1H), 2.56 (m, 1H), 7.49 (m, 1H), 7.63 (dd, 2H), 12.16 (s, 1H), 13.11 (s, 1H).

Derivatives of the Intermediate 10

$R^1$=2,5-Difluorophenyl

Example 116

4-[5-cyano-4-(2,5-difluorophenyl)-1,3-thiazol-2-ylcarbamoyl]-4-methylpentanoic Acid NMR (300 MHz, DMSO-$d_6$): δ=1.26 (s, 6H), 1.94 (m, 2H), 2.15 (m, 2H), 7.53 (m, 3H), 12.15 (s, 1H), 12.88 (s, 1H).

Example 117

Cis-3-[5-cyano-4-(2,5-difluorophenyl)-1,3-thiazol-2-ylcarbamoyl]cyclohexanecarboxylic Acid The compound has been synthesized using the anhydride as acylating agent.
NMR (300 MHz, DMSO-$d_6$): δ=1.34 (m, 3H), 1.47 (q, 1H), 1.90 (m, 3H), 2.09 (d, 1H), 2.28 (m, 1H), 2.63 (m, 1H), 7.54 (m, 3H), 12.15 (s, 1H), 13.11 (s, 1H).

Example 118

4-[5-cyano-4-(2,5-difluorophenyl)-1,3-thiazol-2-ylcarbamoyl]cyclohexanecarboxylic Acid NMR (300 MHz, DMSO-$d_6$): δ=1.50 (m, 4H), 1.96 (t, 4H), 2.23 (t, 1H), 2.56 (m, 1H), 7.53 (m, 3H), 12.15 (s, 1H), 13.10 (s, 1H).

Derivatives of the Intermediate 11

$R^1$=3-(Trifluoromethyl)Phenyl

Example 119

Cis-3-[5-cyano-4-(3-trifluoromethylphenyl)-1,3-thiazol-2-ylcarbamoyl]cyclohexanecarboxylic Acid The compound has been synthesized using the anhydride as acylating agent.
NMR (300 MHz, DMSO-$d_6$): δ=1.33 (m, 3H), 1.49 (m, 1H), 1.91 (m, 3H), 2.11 (m, 1H), 2.30 (m, 1H), 2.64 (m, 1H), 7.87 (t, 1H), 7.93 (d, 1H), 8.31 (s, 1H), 8.34 (d, 1H), 12.26 (s, 1H), 13.13 (s, 1H).

Example 120

4-[5-cyano-4-(3-trifluoromethylphenyl)-1,3-thiazol-2-ylcarbamoyl]cyclohexanecarboxylic Acid NMR (300 MHz, DMSO-$d_6$): δ=1.48 (m, 4H), 1.97 (t, 4H), 2.23 (t, 1H), 2.55 (m, 1H), 7.87 (t, 1H), 7.93 (d, 1H), 8.31 (s, 1H), 8.34 (d, 1H), 12.16 (s, 1H), 13.12 (s, 1H).

Example 121

4-[5-cyano-4-(3-trifluoromethylphenyl)-1,3-thiazol-2-ylcarbamoyl]bicyclo[2.2.2]octane-1-carboxylic Acid NMR (300 MHz, DMSO-$d_6$): δ=1.48 (m, 6H), 1.84 (m, 6H), 7.87 (t, 1H), 7.93 (d, 1H), 8.31 (s, 1H), 8.34 (d, 1H), 12.08 (s, 1H), 13.12 (s, 1H).

Derivatives of the Intermediate 12

$R^1$=Pyridin-4-Yl

Example 122

Cis-3-[5-cyano-4-(pyridin-4-yl)-1,3-thiazol-2-ylcarbamoyl]cyclohexane Carboxylic Acid The compound has been synthesized using the anhydride as acylating agent.
NMR (300 MHz, DMSO-$d_6$): δ=1.33 (m, 3H), 1.48 (q, 1H), 1.90 (m, 3H), 2.09 (d, 1H), 2.28 (m, 1H), 2.63 (m, 1H), 7.44 (d, 2H), 8.59 (d, 2H), 12.18 (s, 1H), 13.07 (s, 1H).

Example 123

4-[5-cyano-4-(pyridin-4-yl)-1,3-thiazol-2-ylcarbamoyl]cyclohexane Carboxylic Acid NMR (300 MHz, DMSO-$d_6$): δ=1.48 (m, 4H), 1.96 (t, 4H), 2.23 (t, 1H), 2.56 (m, 1H), 7.44 (d, 2H), 8.59 (d, 2H), 12.16 (s, 1H), 13.08 (s, 1H).

Example 124

4-[5-cyano-4-(pyridin-4-yl)-1,3-thiazol-2-ylcarbamoyl]bicyclo[2.2.2]octane-1-carboxylic Acid NMR (300 MHz, DMSO-$d_6$): δ=1.46 (m, 6H), 1.85 (m, 6H), 7.46 (d, 2H), 8.60 (d, 2H), 12.08 (s, 1H), 13.10 (s, 1H).

Derivatives of the Intermediate 13

$R^1$=Pyridyn-3-Yl

Example 125

4-[5-cyano-4-(pyridin-3-yl)-1,3-thiazol-2-ylcarbamoyl]-4-methyl Pentanoic Acid

NMR (300 MHz, DMSO-$d_6$): δ=1.25 (s, 6H), 1.94 (m, 2H), 2.12 (m, 2H), 7.63 (q, 1H), 8.33 (d, 1H), 8.73 (d, 1H), 9.16 (s, 1H), 12.16 (s, 1H), 12.85 (s, 1H).

Example 126

Cis-3-[5-Cyano-4-(pyridin-3-yl)-1,3-thiazol-2-ylcarbamoyl]cyclohexane Carboxylic Acid The compound has been synthesized using the anhydride as acylating agent.
NMR (300 MHz, DMSO-$d_6$): δ=1.33 (m, 3H), 1.48 (m, 1H), 1.90 (m, 3H), 2.09 (m, 1H), 2.28 (m, 1H), 2.63 (m, 1H), 7.63 (q, 1H), 8.33 (d, 1H), 8.73 (d, 1H), 9.16 (s, 1H), 12.19 (s, 1H), 13.09 (s, 1H).

Example 127

4-[5-Cyano-4-(pyridin-3-yl)-1,3-thiazol-2-ylcarbamoyl]cyclohexane Carboxylic Acid NMR (300 MHz, DMSO-$d_6$): δ=1.47 (m, 4H), 1.95 (t, 4H), 2.23 (t, 1H), 2.56 (m, 1H), 7.63 (q, 1H), 8.33 (d, 1H), 8.73 (d, 1H), 9.16 (s, 1H), 12.16 (s, 1H), 13.10 (s, 1H).

Derivatives of the Intermediate 14

$R^1$=Pyridyn-2-Yl

Example 128

4-[5-cyano-4-(pyridin-2-yl)-1,3-thiazol-2-ylcarbamoyl]-4-methyl Pentanoic Acid

NMR (300 MHz, DMSO-$d_6$): δ=1.25 (s, 6H), 1.94 (m, 2H), 2.12 (m, 2H), 7.52 (m, 1H), 8.03 (m, 2H), 8.74 (m, 1H), 12.13 (s, 1H), 12.84 (s, 1H).

Example 129

Cis-3-[5-Cyano-4-(pyridin-2-yl)-1,3-thiazol-2-ylcarbamoyl]cyclohexane Carboxylic Acid The compound has been synthesized using the anhydride as acylating agent.

NMR (300 MHz, DMSO-$d_6$): δ=1.34 (m, 3H), 1.48 (q, 1H), 1.83 (m, 1H), 1.90 (m, 2H), 2.09 (d, 1H), 2.28 (m, 1H), 2.63 (m, 1H), 7.52 (m, 1H), 8.03 (m, 2H), 8.74 (m, 1H), 12.17 (s, 1H), 13.05 (s, 1H).

Example 130

4-[5-Cyano-4-(pyridin-2-yl)-1,3-thiazol-2-ylcarbamoyl]cyclohexane Carboxylic Acid NMR (300 MHz, DMSO-$d_6$): δ=1.47 (m, 4H), 1.95 (t, 4H), 2.23 (t, 1H), 2.67 (m, 1H), 7.52 (m, 1H), 8.03 (m, 2H), 8.74 (m, 1H), 12.15 (s, 1H), 13.09 (s, 1H).

Derivatives of the Intermediate 15

$R^1$=Furan-2-Yl

Example 131

4-[5-cyano-4-(furan-2-yl)-1,3-thiazol-2-ylcarbamoyl]-4-methyl Pentanoic Acid

NMR (300 MHz, DMSO-$d_6$): δ=1.22 (s, 6H), 1.92 (m, 2H), 2.10 (m, 2H), 6.76 (q, 1H), 7.08 (dd, 1H), 7.99 (dd, 1H), 12.14 (s, 1H), 12.85 (s, 1H).

Example 132

Cis-3-[5-cyano-4-(furan-2-yl)-1,3-thiazol-2-ylcarbamoyl]cyclohexane Carboxylic Acid The compound has been synthesized using the anhydride as acylating agent.

NMR (300 MHz, DMSO-$d_6$): δ=1.32 (m, 3H), 1.49 (q, 1H), 1.90 (m, 3H), 2.09 (d, 1H), 2.28 (m, 1H), 2.63 (m, 1H), 6.76 (q, 1H), 7.08 (dd, 1H), 7.99 (dd, 1H), 12.23 (s, 1H), 13.10 (s, 1H).

Example 133

4-[5-cyano-4-(furan-2-yl)-1,3-thiazol-2-ylcarbamoyl]cyclohexane Carboxylic Acid

NMR (300 MHz, DMSO-$d_6$): δ=1.47 (m, 4H), 1.97 (m, 4H), 2.24 (m, 1H), 2.58 (m, 1H), 6.76 (q, 1H), 7.08 (dd, 1H), 7.99 (dd, 1H), 12.15 (s, 1H), 13.10 (s, 1H).

Derivatives of the Intermediate 16

$R^1$=4-(Methyl)Furan-3-Yl

Example 134

4-[5-cyano-4-(4-methylfuran-3-yl)-1,3-thiazol-2-ylcarbamoyl]-4-methylpentanoic Acid NMR (300 MHz, DMSO-$d_6$): δ=1.24 (s, 6H), 1.91 (m, 2H), 2.10 (m, 2H), 2.61 (s, 3H), 6.92 (s, 1H), 7.71 (s, 1H), 12.16 (s, 1H), 12.88 (s, 1H).

Example 135

Cis-3-[5-cyano-4-(4-methylfuran-3-yl)-1,3-thiazol-2-ylcarbamoyl]cyclohexanecarboxylic Acid The compound has been synthesized using the anhydride as acylating agent.

NMR (300 MHz, DMSO-$d_6$): δ=1.32 (m, 3H), 1.49 (m, 1H), 1.90 (m, 3H), 2.09 (m, 1H), 2.28 (m, 1H), 2.61 (s, 3H), 2.63 (m, 1H), 6.92 (s, 1H), 7.71 (s, 1H), 12.22 (s, 1H), 13.11 (s, 1H).

Example 136

4-[5-cyano-4-(4-methylfuran-3-yl)-1,3-thiazol-2-ylcarbamoyl]cyclohexanecarboxylic Acid NMR (300 MHz, DMSO-$d_6$): δ=1.48 (m, 4H), 1.97 (m, 4H), 2.24 (m, 1H), 2.57 (m, 1H), 2.61 (s, 3H), 6.92 (s, 1H), 7.71 (s, 1H), 12.16 (s, 1H), 13.09 (s, 1H).

The invention claimed is:

1. A compound of formula (I):

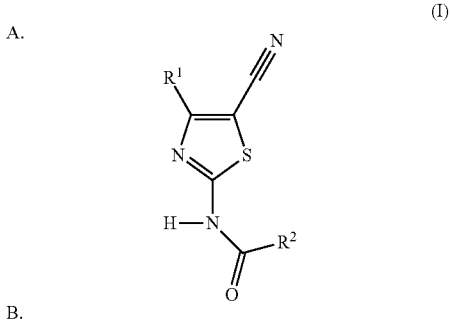

wherein
$R^1$ represents an aryl group;
$R^2$ represents a cycloalkyl group substituted by one or more carboxylic groups (—COOH).

2. A compound according to claim 1 wherein $R^1$ represents a monocyclic aryl.

3. A compound according to claim 2 wherein $R^1$ represents a phenyl.

4. A compound according to claim 3 wherein $R^2$ represents a cycloalkyl group from 4 to 7 carbon atoms substituted by one carboxylic group (—COOH).

5. A compound according to claim 3 wherein $R^2$ represents a cycloalkylalkyl group from 5 to 12 carbon atoms substituted by one carboxylic group (—COOH).

6. A compound according to claim 1 which is one of:

5-(5-cyano-4-phenyl-1,3-thiazol-2-ylcarbamoyl)cyclohexane-1,3-dicarboxylic acid
(1R,3S)-3-(5-cyano-4-phenyl-1,3-thiazol-2-ylcarbamoyl)cyclopentane carboxylic acid
3-(5-cyano-4-phenyl-1,3-thiazol-2-ylcarbamoyl)cyclopentane carboxylic acid
cis-2-(5-cyano-4-phenyl-1,3-thiazol-2-ylcarbamoyl)cyclohexane carboxylic acid
trans-2-(5-cyano-4-phenyl-1,3-thiazol-2-ylcarbamoyl)cyclohexane carboxylic acid
cis-3-(5-cyano-4-phenyl-1,3-thiazol-2-ylcarbamoyl)cyclohexane carboxylic acid
trans-3-(5-cyano-4-phenyl-1,3-thiazol-2-ylcarbamoyl)cyclohexane carboxylic acid
cis-4-(5-cyano-4-phenyl-1,3-thiazol-2-ylcarbamoyl)cyclohexane carboxylic acid
trans-4-(5-cyano-4-phenyl-1,3-thiazol-2-ylcarbamoyl)cyclohexane carboxylic acid
3-(5-cyano-4-phenyl-1,3-thiazol-2-ylcarbamoyl)cyclohexanecarboxylic acid
4-(5-cyano-4-phenyl-1,3-thiazol-2-ylcarbamoyl)cyclohexanecarboxylic acid
4-(5-cyano-4-phenyl-1,3-thiazol-2-ylcarbamoyl)bicyclo[2.2.2]octane-1-carboxylic acid
3-[4-(2-chlorophenyl)-5-cyano-1,3-thiazol-2-ylcarbamoyl]cyclohexane carboxylic acid
4-[4-(2-chlorophenyl)-5-cyano-1,3-thiazol-2-ylcarbamoyl]cyclohexane carboxylic acid
cis-3-[4-(3-chlorophenyl)-5-cyano-1,3-thiazol-2-ylcarbamoyl]cyclopentanecarboxylic acid
trans-3-[4-(3-chlorophenyl)-5-cyano-1,3-thiazol-2-ylcarbamoyl]cyclopentanecarboxylic acid
cis-2-[4-(3-chlorophenyl)-5-cyano-1,3-thiazol-2-ylcarbamoyl]cyclohexanecarboxylic acid
trans-2-[4-(3-chlorophenyl)-5-cyano-1,3-thiazol-2-ylcarbamoyl]cyclohexane carboxylic acid
cis-3-[4-(3-chlorophenyl)-5-cyano-1,3-thiazol-2-ylcarbamoyl]cyclohexanecarboxylic acid
trans-3-[4-(3-chlorophenyl)-5-cyano-1,3-thiazol-2-ylcarbamoyl]cyclohexane carboxylic acid
cis-4-[4-(3-chlorophenyl)-5-cyano-1,3-thiazol-2-ylcarbamoyl]cyclohexane carboxylic acid
trans-4-[4-(3-chlorophenyl)-5-cyano-1,3-thiazol-2-ylcarbamoyl]cyclohexane carboxylic acid
3-[4-(3-chlorophenyl)-5-cyano-1,3-thiazol-2-ylcarbamoyl]cyclohexane carboxylic acid
4-[4-(3-chlorophenyl)-5-cyano-1,3-thiazol-2-ylcarbamoyl]cyclohexane carboxylic acid
4-[4-(3-chlorophenyl)-5-cyano-1,3-thiazol-2-ylcarbamoyl]bicyclo[2.2.2]octane-1-carboxylic acid
cis-3-[5-cyano-4-(2-fluorophenyl)-1,3-thiazol-2-ylcarbamoyl]cyclopentanecarboxylic acid
trans-3-[5-cyano-4-(2-fluorophenyl)-1,3-thiazol-2-ylcarbamoyl]cyclopentane carboxylic acid
cis-2-[5-cyano-4-(2-fluorophenyl)-1,3-thiazol-2-ylcarbamoyl]cyclohexanecarboxylic acid
trans-2-[5-cyano-4-(2-fluorophenyl)-1,3-thiazol-2-ylcarbamoyl]cyclohexane carboxylic acid
cis-3-[5-cyano-4-(2-fluorophenyl)-1,3-thiazol-2-ylcarbamoyl]cyclohexanecarboxylic acid
trans-3-[5-cyano-4-(2-fluorophenyl)-1,3-thiazol-2-ylcarbamoyl]cyclohexane carboxylic acid
cis-4-[5-cyano-4-(2-fluorophenyl)-1,3-thiazol-2-ylcarbamoyl]cyclohexanecarboxylic acid
trans-4-[5-cyano-4-(2-fluorophenyl)-1,3-thiazol-2-ylcarbamoyl]cyclohexane carboxylic acid
3-[5-cyano-4-(2-fluorophenyl)-1,3-thiazol-2-ylcarbamoyl]cyclohexane carboxylic acid
4-[5-cyano-4-(2-fluorophenyl)-1,3-thiazol-2-ylcarbamoyl]cyclohexane carboxylic acid
4-[5-cyano-4-(2-fluorophenyl)-1,3-thiazol-2-ylcarbamoyl]bicyclo[2.2.2]octane-1-carboxylic acid
cis-3-[5-cyano-4-(3-fluorophenyl)-1,3-thiazol-2-ylcarbamoyl]cyclopentanecarboxylic acid
trans-3-[5-cyano-4-(3-fluorophenyl)-1,3-thiazol-2-ylcarbamoyl]cyclopentane carboxylic acid
cis-2-[5-cyano-4-(3-fluorophenyl)-1,3-thiazol-2-ylcarbamoyl]cyclohexanecarboxylic acid
trans-2-[5-cyano-4-(3-fluorophenyl)-1,3-thiazol-2-ylcarbamoyl]cyclohexane carboxylic acid
cis-3-[5-cyano-4-(3-fluorophenyl)-1,3-thiazol-2-ylcarbamoyl]cyclohexanecarboxylic acid
trans-3-[5-cyano-4-(3-fluorophenyl)-1,3-thiazol-2-ylcarbamoyl]cyclohexane carboxylic acid
cis-4-[5-cyano-4-(3-fluorophenyl)-1,3-thiazol-2-ylcarbamoyl]cyclohexanecarboxylic acid
trans-4-[5-cyano-4-(3-fluorophenyl)-1,3-thiazol-2-ylcarbamoyl]cyclohexane carboxylic acid
3-[5-cyano-4-(3-fluorophenyl)-1,3-thiazol-2-ylcarbamoyl]cyclohexane carboxylic acid
4-[5-cyano-4-(3-fluorophenyl)-1,3-thiazol-2-ylcarbamoyl]cyclohexane carboxylic acid
4-[5-cyano-4-(3-fluorophenyl)-1,3-thiazol-2-ylcarbamoyl]bicyclo[2.2.2]octane-1-carboxylic acid
cis-3-[5-cyano-4-(4-fluorophenyl)-1,3-thiazol-2-ylcarbamoyl]cyclopentanecarboxylic acid
trans-3-[5-cyano-4-(4-fluorophenyl)-1,3-thiazol-2-ylcarbamoyl]cyclopentane carboxylic acid
cis-2-[5-cyano-4-(4-fluorophenyl)-1,3-thiazol-2-ylcarbamoyl]cyclohexanecarboxylic acid
trans-2-[5-cyano-4-(4-fluorophenyl)-1,3-thiazol-2-ylcarbamoyl]cyclohexane carboxylic acid
cis-3-[5-cyano-4-(4-fluorophenyl)-1,3-thiazol-2-ylcarbamoyl]cyclohexanecarboxylic acid
trans-3-[5-cyano-4-(4-fluorophenyl)-1,3-thiazol-2-ylcarbamoyl]cyclohexane carboxylic acid
cis-4-[5-cyano-4-(4-fluorophenyl)-1,3-thiazol-2-ylcarbamoyl]cyclohexanecarboxylic acid
trans-4-[5-cyano-4-(4-fluorophenyl)-1,3-thiazol-2-ylcarbamoyl]cyclohexane carboxylic acid
3-[5-cyano-4-(4-fluorophenyl)-1,3-thiazol-2-ylcarbamoyl]cyclohexane carboxylic acid
4-[5-cyano-4-(4-fluorophenyl)-1,3-thiazol-2-ylcarbamoyl]cyclohexane carboxylic acid
4-[5-cyano-4-(4-fluorophenyl)-1,3-thiazol-2-ylcarbamoyl]bicyclo[2.2.2]octane-1-carboxylic acid
3-[5-cyano-4-(3,4-difluorophenyl)-1,3-thiazol-2-ylcarbamoyl]cyclohexanecarboxylic acid
4-[5-cyano-4-(3,4-difluorophenyl)-1,3-thiazol-2-ylcarbamoyl]cyclohexanecarboxylic acid
3-[5-cyano-4-(3,5-difluorophenyl)-1,3-thiazol-2-ylcarbamoyl]cyclohexanecarboxylic acid
4-[5-cyano-4-(3,5-difluorophenyl)-1,3-thiazol-2-ylcarbamoyl]cyclohexanecarboxylic acid 3-[5-cyano-4-(3-trifluoromethylphenyl)-1,3-thiazol-2-yl-carbamoyl]cyclohexane carboxylic acid 4-[5-cyano-4-(3-trifluoromethylphenyl)-1,3-thiazol-2-yl-carbamoyl]bicyclo[2.2.2]octane-1-carboxylic acid.

7. A pharmaceutical composition comprising a compound as defined in claim 1 mixed with a pharmaceutically acceptable diluent or carrier.

8. A combination product comprising a compound according to claim 1; and another compound selected from (a) angiotensin converting enzyme inhibitors (ACE-inhibitors) (b) angiotensin receptor antagonists (ARB), (c) statins, (d) beta blockers, (e) calcium antagonists and (f) diuretics, (g) leukotriene antagonists, (h) corticosteroids, (i) aldosterone antagonists, (j) histamine antagonists, (k) CRTh2 antagonists, (l) renin inhibitors, (m) vasopresin antagonists.

9. A compound according to claim 1 wherein the aryl group is substituted by one or more substituents selected from the group consisting of halogen atoms.

10. A compound according to claim 1 wherein the cycloalkyl group is substituted by one or more halogen atoms.

* * * * *